US008362030B2

(12) United States Patent
Ingenito et al.

(10) Patent No.: US 8,362,030 B2
(45) Date of Patent: Jan. 29, 2013

(54) TRICYCLIC DERIVATIVES AS INHIBITORS OF POLY(ADP-RIBOSE) POLYMERASE (PARP)

(75) Inventors: Raffaele Ingenito, Pomezia (IT); Philip Jones, Pomezia (IT); Laura Llauger Bufi, Pomezia (IT); Jesus Maria Ontoria Ontoria, Pomezia (IT); Rita Scarpelli, Pomezia (IT)

(73) Assignee: Istituto di Ricerche di Biologia Molecolare P. Angeletti S.R.L., Rome (IT)

( * ) Notice: Subject to any disclaimer, the term of this patent is extended or adjusted under 35 U.S.C. 154(b) by 86 days.

(21) Appl. No.: 12/922,270

(22) PCT Filed: Mar. 13, 2009

(86) PCT No.: PCT/GB2009/000661
§ 371 (c)(1),
(2), (4) Date: Nov. 17, 2010

(87) PCT Pub. No.: WO2009/112832
PCT Pub. Date: Sep. 17, 2009

(65) Prior Publication Data
US 2011/0053911 A1    Mar. 3, 2011

(30) Foreign Application Priority Data
Mar. 14, 2008    (GB) .................................. 0804755.7

(51) Int. Cl.
*A61K 31/437* (2006.01)
*C07D 471/12* (2006.01)
(52) U.S. Cl. ........ 514/293; 540/484; 540/553; 540/557; 546/26; 546/79; 546/82; 514/279; 514/290; 514/292
(58) Field of Classification Search .................. 544/336, 544/344, 346; 546/112, 113, 26, 79, 80, 546/82; 514/252.1, 299, 300, 279, 290, 292, 514/293; 540/484, 553, 555, 557
See application file for complete search history.

(56) References Cited

U.S. PATENT DOCUMENTS

| | | | | |
|---|---|---|---|---|
| 5,958,942 | A * | 9/1999 | Takatani et al. ............... | 514/292 |
| 6,251,905 | B1 * | 6/2001 | Takatani et al. ........... | 514/253.03 |
| 7,834,015 | B2 * | 11/2010 | Jones et al. .................... | 514/249 |

FOREIGN PATENT DOCUMENTS

| EP | 0826686 | 4/1998 |
|---|---|---|
| WO | WO 96/02542 | 2/1996 |
| WO | WO 98/29136 | 7/1998 |
| WO | WO 00/42040 | 7/2000 |
| WO | WO01/16136 | 3/2001 |
| WO | WO 01/57038 | 8/2001 |
| WO | WO 02/42306 | 5/2002 |
| WO | WO 2004/087713 | 10/2004 |
| WO | WO 2005/012305 | 2/2005 |
| WO | WO 2007/113596 | 10/2007 |
| WO | WO 2008/001134 | 1/2008 |
| WO | WO 2008/017883 | 2/2008 |

OTHER PUBLICATIONS

Bryant, Helen E. et al., "Specific Killing of BRCA2-deficient tumours with inhibitors of poly(ADP-Ribose) polymerase", Nature, 434:913-916 (Apr. 14, 2005).
Farmer, Hannah, et al., "Targeting the DNA repair defect in BRCA mutant cells as a therapeutic strategy", Nature 434:917-921 (Apr. 14, 2005).
Koch, Stacie S. Canan, et al., "Novel Tricyclic Poly(ADP-ribose) Polymerase-1 Inhibitors with Potent Anticancer Chemopotentiating Activity: Design, Synthesis, and X-ray Cocrystal Structure", J. Med. Chem 45:4961-4974 (2002).
Skalitzky, Donald J., et al., "Tricyclic Benzimidazoles as Potent Poly(ADP-ribose) Polymerase-1 Inhibitors", J. Med. Chem. 46:210-213 (2003).
Tikhe, Jayashree G., et al., "Design, Synthesis, and Evaluation of 3,4-Dihydro-2H-[1,4]diazepino[6,7,1-hi]indol-1-ones as Inhibitors of Poly(ADP-Ribose) Polymerase", J. Med. Chem. 47:5467-5481 (2004).

* cited by examiner

*Primary Examiner* — Golam M M Shameem
(74) *Attorney, Agent, or Firm* — Yong Zhao; David A. Muthard; Matthew A. Leff

(57) ABSTRACT

The present invention relates to compounds of formula (I) and pharmaceutically acceptable salts or tautomers thereof which are inhibitors of poly(ADP-ribose)polymerase (PARP) and thus useful for the treatment of cancer, inflammatory diseases, reperfusion injuries, ischaemic conditions, stroke, renal failure, cardiovascular diseases, vascular diseases other than cardiovascular diseases, diabetes mellitus, neurodegenerative diseases, retroviral infections, retinal damage, skin senescence and UV-induced skin damage, and as chemo- or radiosensitizers for cancer treatment.

11 Claims, No Drawings

TRICYCLIC DERIVATIVES AS INHIBITORS OF POLY(ADP-RIBOSE) POLYMERASE (PARP)

The present invention relates to tricyclic derivatives which are inhibitors of the enzyme poly(ADP-ribose)polymerase (PARP), previously known as poly(ADP-ribose)synthase and poly(ADP-ribosyl)transferase. Compounds of the present invention are useful as mono-therapies in tumors with specific defects in DNA-repair pathways and as enhancers of certain DNA-damaging agents such as anticancer agents and radiotherapy. Furthermore, compounds of the present invention are useful for reducing cell necrosis (in stroke and myocardial infarction), down regulating inflammation and tissue injury, treating retroviral infections and protecting against the toxicity of chemotherapy.

Poly(ADP-ribose)polymerase (PARP) constitute a super family of eighteen proteins containing PARP catalytic domains (*Bioessays* (2004) 26:1148). These proteins include PARP-1, PARP-2, PARP-3, tankyrase-1, tankyrase-2, vault-PARP and TiPARP. PARP-1, the founding member, consists of three main domains: an amino (N)-terminal DNA-binding domain (DBD) containing two zinc fingers, the automodification domain, and a carboxy (C)-terminal catalytic domain.

PARP are nuclear and cytoplasmic enzymes that cleave $NAD^+$ to nicotinamide and ADP-ribose to form long and branched ADP-ribose polymers on target proteins, including topoisomerases, histones and PARP itself (*Biochem. Biophys. Res. Commun.* (1998) 245:1-10).

Poly(ADP-ribosyl)ation has been implicated in several biological processes, including DNA repair, gene transcription, cell cycle progression, cell death, chromatin functions and genomic stability.

The vast majority of PARP inhibitors to date interact with the nicotinamide binding domain of the enzyme and behave as competitive inhibitors with respect to $NAD^+$ (*Expert Opin. Ther. Patents* (2004) 14:1531-1551). Structural analogues of nicotinamide, such as benzamide and derivatives were among the first compounds to be investigated as PARP inhibitors. However, these molecules have a weak inhibitory activity and possess other effects unrelated to PARP inhibition. Thus, there is a need to provide potent inhibitors of the PARP enzyme.

Compounds of this invention are useful in the inhibition of poly(ADP-ribose)polymerase (PARP). They are particularly useful as inhibitors of PARP-1 and/or PARP-2. The present invention provides compounds of formula I:

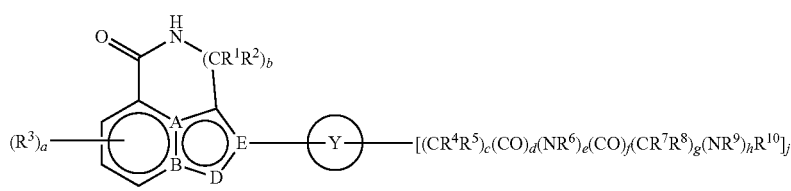

(I)

wherein:
a is 0, 1, 2 or 3;
b is 1 or 2;
each c is independently 0, 1, 2, 3, 4, 5 or 6;
each d is independently 0 or 1;
each e is independently 0 or 1;
each f is independently 0 or 1;
each g is independently 0, 1, 2, 3, 4, 5 or 6;
each h is independently 0 or 1;
j is 0, 1, 2 or 3;
one of A, B, D and E is N and the others are independently N or either C or CH as the case may be, provided that when D is N then at least one of A, B and E is N;
each of $R^1$ and $R^2$ is independently hydrogen or $C_{1-6}$alkyl;
each $R^3$ is independently hydroxy, halogen, cyano, halo$C_{1-6}$ alkyl, $C_{1-6}$alkoxy or halo$C_{1-6}$alkoxy;
each of $R^4$, $R^5$, $R^7$ and $R^8$ is independently hydrogen, $C_{1-6}$alkyl or halo $C_{1-6}$alkyl;
each of $R^6$ and $R^9$ is independently hydrogen, $C_{1-6}$alkyl or $C_{3-10}$cycloalkyl;
each $R^{10}$ is independently hydrogen, hydroxy, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_{1-6}$alkoxy, $C_{1-6}$alkoxycarbonyl, carboxy, nitro or a ring which is: $C_{6-10}$aryl; $C_{6-10}$aryloxy; $C_{6-10}$-arylcarbonyl; $C_{3-10}$cycloalkyl; oxetanyl; azetidinyl; a 5 or 6 membered saturated or partially saturated heterocyclic ring containing one, two or three heteroatoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 N atoms; or a 7-15 membered unsaturated, partially saturated or saturated heterocyclic ring containing 1, 2, 3 or 4 heteroatoms independently selected from N, O and S; any of which rings being optionally substituted by one, two or three groups independently selected from $(CH_2)_xR^{11}$;
each x is independently 0, 1, 2, 3, 4, 5 or 6;
each $R^{11}$ is independently hydroxy, oxo, cyano, halogen, $C_{1-6}$alkyl, $C_{2-10}$alkenyl, $C_{1-6}$alkylcarbonyl, $C_{1-6}$alkoxy, halo$C_{1-6}$alkoxy, hydroxy$C_{1-6}$alkyl, $C_{1-6}$alkoxycarbonyl, carboxy, $NR^aR^b$, $CONR^aR^b$, $S(O)_rR^e$ or a ring which is: $C_{6-10}$aryl; $C_{6-10}$aryl$C_{1-6}$alkyl; oxetanyl; azetidinyl; a 5, 6 or 7 membered saturated or partially saturated heterocyclic ring containing one, two or three heteroatoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-10 membered unsaturated or partially saturated heterocyclic ring containing 1, 2, 3 or 4 heteroatoms independently selected from N, O and S; any of which rings being optionally substituted by one, two or three groups independently selected from hydroxy, cyano, halogen, $C_{1-6}$alkyl, $C_{1-6}$alkoxy, $C_{2-10}$alkenyl, halo$C_{1-6}$alkyl, amino, $C_{1-6}$alkylamino and di($C_{1-6}$alkyl)amino;
each of $R^a$ and $R^b$ is independently hydrogen, $C_{1-6}$alkyl, $C_{1-6}$alkylcarbonyl, halo$C_{1-6}$alkyl, hydroxy$C_{1-6}$alkyl, $S(O)_r$ $R^c$ or $S(O)_rN(R^d)_2$; or
$R^a$ and $R^b$ together with the N atom to which they are attached form an azetidinyl ring or a 5, 6 or 7 membered saturated or partially saturated heterocycle containing one, two or three N atoms and zero or one O atom, the ring being optionally substituted by one, two or three groups independently selected from hydroxy, cyano, halogen, $C_{1-6}$alkyl, $C_{1-6}$alkoxy, $C_{2-10}$alkenyl and halo$C_{1-6}$alkyl;

r is 0, 1 or 2;

$R^c$ is $C_{1-6}$alkyl, $C_{6-10}$aryl, oxetanyl, azetidinyl, a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-10 membered unsaturated or partially saturated heterocyclic ring containing 1, 2, 3 or 4 heteroatoms independently selected from N, O and S; any of which rings being optionally substituted by one, two or three groups independently selected from hydroxy, cyano, halogen, $C_{1-6}$alkyl, $C_{2-10}$alkenyl and halo$C_{1-6}$alkyl;

each $R^d$ is independently hydrogen or $C_{1-6}$alkyl;

Y is $C_{6-10}$aryl, a 5 membered unsaturated heterocycle containing 1, 2, 3 or 4 heteroatoms independently selected from O, N and S, but not more than one of which is O or S, a 6 membered unsaturated heterocycle containing 1, 2 or 3 N atoms or a 7-10 membered unsaturated heterocyclic ring containing 1, 2, 3 or 4 heteroatoms independently selected from N, O and S; or a pharmaceutically acceptable salt, stereoisomer or tautomer thereof.

In an embodiment A is N, B is C, D is N and E is C; or A is C, B is C, D is N and E is N; or A is C, B is N, D is CH and E is C.

In an embodiment a is 0 or 1. In another embodiment a is 0. In another embodiment a is 1.

In an embodiment b is 1. In another embodiment b is 2.

In an embodiment c is 0, 1 or 2. In another embodiment c is 0 or 1.

In an embodiment d is 0.

In an embodiment e is 0. In another embodiment e is 1.

In an embodiment f is 0. In another embodiment f is 1.

In an embodiment g is 0, 1 or 2.

In an embodiment h is 0. In another embodiment h is 1.

In an embodiment j is 1, 2 or 3. In another embodiment j is 1. In another embodiment j is 0 or 1.

In an embodiment each or $R^1$ and $R^2$ is hydrogen.

In an embodiment $R^3$ is halo$C_{1-6}$alkyl or halogen, particularly halogen.

In an embodiment a is 0 or 1 and $R^3$ is halo$C_{1-6}$allyl or halogen.

A particular $R^3$ group is fluorine.

In an embodiment each $R^9$ is independently hydrogen or $C_{1-6}$alkyl.

A particular $R^9$ group is methyl.

In an embodiment $R^{10}$ is hydroxy, $C_{1-6}$alkyl, $C_{1-6}$alkoxy, nitro or a ring which is: azetidinyl, a 5 or 6 membered saturated or partially saturated heterocyclic ring containing one, two or three heteroatoms independently selected from N, O and S, a 6 membered heteroaromatic ring containing 1, 2 or 3 N atoms or a 7 to 10 membered saturated or partially saturated heterocyclic ring containing 1, 2, 3 or 4 heteroatoms independently selected from N, O and S; any of which rings being optionally substituted by one, two or three groups independently selected from $(CH_2)_xR^{11}$.

In an embodiment $R^{10}$ is hydroxy, $C_{1-6}$alkyl, $C_{1-6}$alkoxy, nitro or a ring which is: diazoniaspirodecanyl, piperidinyl, pyridinyl, pyrrolidinyl, azetidinyl or piperazinyl; any of which rings being optionally substituted by one, two or three groups independently selected from $(CH_2)_xR^{11}$.

In an embodiment when $R^{10}$ is a ring it is unsubstituted or monosubstituted.

In an embodiment x is 0.

In an embodiment $R^{11}$ is $C_{1-6}$alkyl.

In an embodiment x is 0 and $R^{11}$ is $C_{1-6}$alkyl.

A particular $R^{11}$ group is methyl.

Particular $R^{10}$ groups are methyl, isopropyl, diazoniaspiro[4.5]decanyl, methylpiperidinyl, ethoxy, nitro, hydroxy, pyridinyl, pyrrolidinyl, azetidinyl, methylpiperazinyl and piperidinyl.

Specific $R^{10}$ groups are methyl, isopropyl, 2,7-diazoniaspiro[4.5]decan-2-yl, 1-methylpiperidin-4-yl, ethoxy, nitro, hydroxy, pyridin-3-yl, pyridin-2-yl, pyrrolidin-1-yl, azetidin-3-yl, (3S)-1-methylpiperidin-3-yl, (3R)-1-methylpiperidin-3-yl, (2S)-1-methylpiperidin-2-yl, (2R)-1-methylpiperidin-2-yl, 4-methylpiperazin-1-yl, piperidin-3-yl, (3R)-piperidin-3-yl and (3S)-piperidin-3-yl.

In an embodiment Y is $C_{6-10}$aryl.

A particular Y group is phenyl.

In an embodiment each of $R^a$ and $R^b$ is independently hydrogen, $C_{1-6}$alkyl, $C_{1-6}$alkylcarbonyl, halo$C_{1-6}$alkyl, hydroxy$C_{1-6}$alkyl, $S(O)_rR^c$ or $S(O)_rN(R^d)_2$.

In an embodiment each of $R^a$ and $R^b$ is independently hydrogen or $C_{1-6}$alkyl.

In an embodiment $R^c$ is $C_{1-6}$alkyl.

In an embodiment $R^d$ is independently hydrogen or $C_{1-6}$alkyl.

The present invention also provides compounds of formula II:

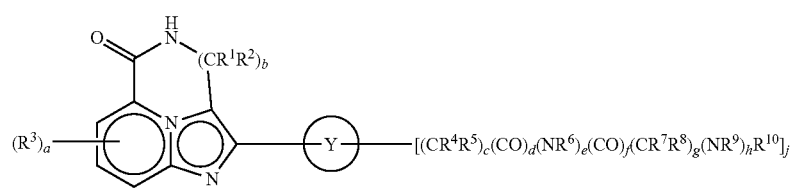

wherein a, b, c, d, e, f, g, h, j, $R^1$, $R^2$, $R^3$, $R^4$, $R^5$, $R^6$, $R^7$, $R^8$, $R^9$, $R^{10}$ and Y are as defined above;

or a pharmaceutically acceptable salt, stereoisomer or tautomer thereof.

In an embodiment each of $R^4$ and $R^5$ is hydrogen.

In an embodiment each $R^6$ is independently hydrogen or $C_{1-6}$alkyl.

Particular $R^6$ groups are hydrogen and methyl.

In an embodiment each of $R^7$ and $R^8$ is hydrogen.

The present invention also provides compounds of formula III:

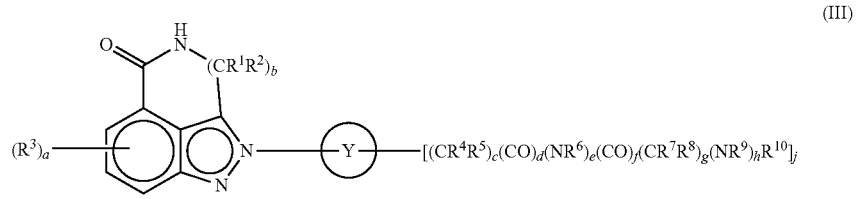

(III)

wherein a, b, c, d, e, f, g, h, j, $R^1, R^2, R^3, R^4, R^5, R^6, R^7, R^8, R^9, R^{10}$ and Y are as defined above;
or a pharmaceutically acceptable salt, stereoisomer or tautomer thereof.

The present invention also provides compounds of formula IV:

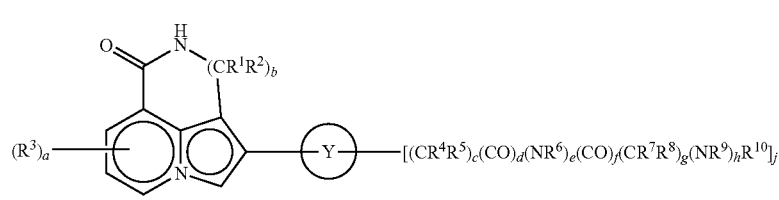

(IV)

wherein a, b, c, d, e, f g, h, j, $R^1, R^2, R^3, R^4, R^5, R^6, R^7, R^8, R^9, R^{10}$ and Y are as defined above;
or a pharmaceutically acceptable salt, stereoisomer or tautomer thereof.

The present invention also provides compounds of formula V:

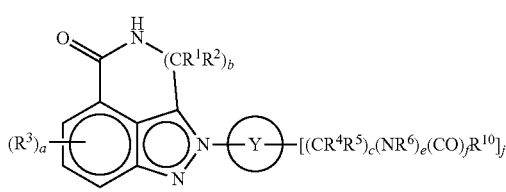

(V)

wherein a, b, c, e, f, j, $R^1, R^2, R^3, R^4, R^5, R^6, R^{10}$ and Y are as defined above;
or a pharmaceutically acceptable salt, stereoisomer or tautomer thereof.

The preferred identities with reference to compounds of any one of formulae II, III, IV and V are as defined previously for formula I mutatis mutandis.

The present invention also includes within its scope N-oxides of the compounds of formula I above. In general, such N-oxides may be formed on any available nitrogen atom. The N-oxides may be formed by conventional means, such as reacting the compound of formula I with oxone in the presence of wet alumina.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

The compounds disclosed herein may exist as tautomers and both tautomeric forms are intended to be encompassed by the scope of the invention, even though only one tautomeric structure may be depicted. For example, compounds of formula I may tautomerise into compounds of the following structure I:

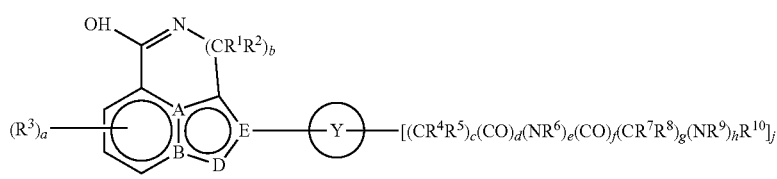

(I)

The compounds may exist in different isomeric forms, all of which are encompassed by the present invention.

The compounds may exist in a number of different polymorphic forms. When any variable (e.g. $R^1$ etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched, straight-chain and cyclic saturated aliphatic hydrocarbon groups having the specified number of carbon atoms. For example, "$C_{1-6}$alkyl" is defined to include groups having 1, 2, 3, 4, 5 or 6 carbons in a linear, branched or cyclic arrangement. For example, "$C_{1-6}$alkyl" specifically includes methyl, ethyl, n-propyl, i-propyl, n-butyl, t-butyl, i-butyl, pentyl, hexyl, cyclopropyl, cyclobutyl, cyclopentyl and cyclohexyl and so on. Preferred alkyl groups are methyl and ethyl. The term "cycloalkyl" means a monocyclic, bicyclic or polycyclic saturated aliphatic hydrocarbon group having the specified number of carbon atoms. For example, "$C_{3-7}$cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclobutyl, cyclopentyl and cyclohexyl.

As used herein, the term "$C_{2-10}$alkenyl" refers to a non-aromatic hydrocarbon radical, straight or branched, containing from 2 to 10, including 2 to 6, carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. Preferred alkenyl groups include ethenyl and propenyl.

As used herein, the term "$C_{2-10}$alkynyl" refers to a hydrocarbon radical straight or branched, containing from containing from 2 to 10, including 2 to 6 carbon atoms and at least one carbon to carbon triple bond. Up to three carbon-carbon triple bonds may be present. Alkynyl groups include ethynyl, propynyl, butyryl, 3-methylbutynyl and so on. Preferred alkynyl groups include ethynyl and propynyl "Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy, t-butoxy, cyclopropyloxy, cyclobutyloxy and cyclopentyloxy. The preferred alkoxy groups are methoxy and ethoxy. The term '$C_{6-10}$aryloxy' can be construed analogously, and an example of this group is phenoxy.

The terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-3}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

As used herein, the term "hydroxy$C_{1-6}$alkyl" means a $C_{1-6}$alkyl group in which one or more (in particular, 1 to 3) hydrogen atoms have been replaced by hydroxy groups. Preferred are $CH_2OH$, $CH_2CHOH$ and $CHOHCH_3$. The term 'hydroxy$C_{2-10}$alkenyl' and 'hydroxy$C_{2-10}$alkynyl' can be construed analogously. An example of 'hydroxy$C_{2-10}$alkynyl' is (hydroxy)(methyl)butynyl.

As used herein, the term "$C_{1-6}$alkylcarbonyl" or "$C_{1-6}$alkoxycarbonyl" denotes a $C_{1-6}$alkyl or $C_{1-6}$alkoxy radical, respectively, attached via a carbonyl (C=O) radical. Suitable examples of $C_{1-6}$alkylcarbonyl groups include methylcarbonyl, ethylcarbonyl, propylcarbonyl, isopropylcarbonyl and tert-butylcarbonyl. Examples of $C_{1-6}$alkoxycarbonyl include methoxycarbonyl, ethoxycarbonyl, propoxycarbonyl, isopropoxycarbonyl and tert-butoxycarbonyl. The term '$C_{6-10}$arylcarbonyl' can be construed analogously, and an example of this group is benzoyl.

The rings present in the compounds of this invention may be monocyclic or multicyclic, particularly bicyclic. The multicyclic rings may be fused, bridged or spiro inked.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl and tetrahydrobenzo[7]annulene. The preferred aryl group is phenyl or naphthyl, especially phenyl.

7-15 membered heterocycles include 7, 8, 9, 10, 11, 12, 13, 14 and 15 membered heterocycles. Similarly, 7-10 membered rings include 7, 8, 9 and 10 membered rings.

Examples of particular heterocycles of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furyl, furazanyl, imidazolyl, indolinyl, indolyl, indolizinyl, indolinyl, isoindolinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl, pyrrolyl, quinazolinyl, quinolinyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidyl, pyridin-2-onyl, pyrrolidinyl, imidazolinyl, imidazolidinyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydroisoquinolinyl, dihydrotetrazolyl, dihydrothiadiazolyl, dihydrothiazolyl, dihydrothienyl, dihydrotriazolyl, dihydroazetidinyl, dihydroisochromenyl, dihydrochromenyl, dihydroimidazolonyl, dihydrotriazolonyl, dihydrobenzodioxinyl, dihydrothiazolopyrimidinyl, dihydroimidazopyrazinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl, azabicycloheptanyl, chromenonyl, triazolopyrimidinyl, dihydrobenzoxazinyl, thiazolotriazolyl, azoniabicycloheptanyl, azoniabicyclooctanyl, phthalazinyl, naphthyridinyl, pteridinyl, dihydroquinazolinyl, dihydrophthalazinyl, benzisoxazolyl, tetrahydronaphthyridinyl, dibenzo[b,d]furanyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, diazepanyl, azoniabicyclohexanyl, azoniabicycloheptanyl, azepanyl, octahydropyridopyrazinyl, diazabicycloheptanyl diazoniaspirodecanyl, diazoniaspirononanyl, octahydropyrrolopyrrolyl and tetrahydrotriazolopyrazinyl and N-oxides thereof. Attachment of a heterocyclyl substituent can occur via a carbon atom or via a heteroatom.

Preferred 5 or 6 membered saturated or partially saturated heterocycles are pyrrolidinyl, piperidinyl, piperazinyl, morpholinyl, tetrahydrofuran, thiomorpholinyl, azoniabicyclohexanyl, azoniabicycloheptanyl and tetrahydropyranyl.

Preferred 5 membered heteroaromatic rings are thienyl, thiazolyl, pyrazolyl, isoxazolyl, isothiazolyl, imidazolyl, thiadiazolyl, oxazolyl, oxadiazolyl, triazolyl, tetrazolyl, furyl and pyrrolyl.

Preferred 6 membered heteroaromatic rings are pyridinyl, pyrimidinyl, pyridazinyl and pyrazinyl.

Preferred 7-15 membered saturated, partially saturated or unsaturated heterocyclic rings are diazepanyl, azepanyl, tetrahydroquinolinyl, quinolinyl, indolyl, imidazopyridinyl, benzothiazolyl, quinoxalinyl, benzothiadiazolyl, benzoxazolyl, dihydrobenzodioxinyl, benzodioxolyl, dihydroisoindolyl, dihydroindolyl, tetrahydroisoquinolinyl, isoquinolinyl, benzoisothiazolyl, dihydroimidazopyrazinyl, benzothienyl, benzoxadiazolyl, thiazolotriazolyl, dihydrothiazolopyrimidinyl, dihydrobenzoxazinyl, dihydrobenzofuranyl, benzimidazolyl, benzofuranyl, dihydrobenzoxazolyl, dihydroquinazolinyl, dihydrophthalazinyl, indazolyl, benzisoxazolyl, tetrahydronaphthyridinyl, triazolopyrimidinyl, dibenzo[b,d]furanyl, naphthyridinyl, dihydroquinolinyl, dihydroisochromenyl, dihydrochromenyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, quinazolinyl, indolizinyl, octahydropyridopyrazinyl, diazabicycloheptanyl, diazoniaspirodecanyl, diazoniaspirononanyl, octahydropyrrolopyrrolyl and tetrahydrotriazolopyrazinyl.

As used herein, the term "halogen" refers to fluorine, chlorine, bromine and iodine, of which fluorine and chlorine are preferred.

Particular compounds within the scope of the present invention are:

N-Methyl[4-(6-oxo-6,7,8,9-tetrahydro-2,7,9b-triazabenzo [cd]azulen-1-yl)phenyl]methanaminium trifluoroacetate;

N-Methyl[4-(5-oxo-4,5-dihydro-3H-1,4,8b-triazaacenaphthylen-2-yl)phenyl]methanaminium trifluoroacetate;

N-Methyl[4-(6-oxo-3,4,5,6-tetrahydro-2H-azepino[5,4,3-cd]indazol-2-yl)phenyl]methanaminium trifluoroacetate;

N,N-Dimethyl[4-(6-oxo-3,4,5,6-tetrahydro-2H-azepino[5,4,3-cd]indazol-2-yl)phenyl]methanaminium trifluoroacetate;

$N^2,N^2$-Dimethyl-N-[4-(1-oxo-1,2,3,4-tetrahydroazepino[3,4,5-hi]indolizin-5-yl)phenyl]glycinamide;

3-[4-(8-Fluoro-6-oxo-3,4,5,6-tetrahydro-2H-azepino[5,4,3-cd]indazol-2-yl)phenyl]piperidinium trifluoroacetate;

8-fluoro-2-{4-[(3R)-piperidin-3-yl]phenyl}-2,3,4,5-tetrahydro-6H-azepino[5,4,3-cd]indazol-6-one;

8-fluoro-2-{4-[(3S)-piperidin-3-yl]phenyl}-2,3,4,5-tetrahydro-6H-azepino[5,4,3-cd]indazol-6-one;

N,N-dimethyl[4-(6-oxo-6,7,8,9-tetrahydro-2,7,9b-triazabenzo[cd]azulen-1-yl)phenyl]methanaminium trifluoroacetate;

N-[4-(6-oxo-6,7,8,9-tetrahydro-2,7,9b-triazabenzo[cd]azulen-1-yl)benzyl]propan-2-aminium trifluoroacetate;

2-[4-(6-oxo-6,7,8,9-tetrahydro-2,7,9b-triazabenzo[cd]azulen-1-yl)benzyl]-2,7-diazoniaspiro[4.5]decane bis(trifluoroacetate);

1-methyl-4-({[4-(6-oxo-6,7,8,9-tetrahydro-2,7,9b-triazabenzo[cd]azulen-1-yl)benzyl]ammonio}methyl)piperidinium bis(trifluoroacetate);

N,N-dimethyl[4-(5-oxo-4,5-dihydro-3H-1,4,8b-triazaacenaphthylen-2-yl)phenyl]methanaminium trifluoroacetate;

2-[4-(5-oxo-4,5-dihydro-3H-1,4,8b-tiazaacenaphthylen-2-yl)benzyl]-2,7-diazoniaspiro[4.5]decane bis(trifluoroacetate);

1-methyl-4-({[4-(5-oxo-4,5-dihydro-3H-1,4,8b-triazaacenaphthylen-2-yl)benzyl]ammonio}methyl)piperidinium bis(trifluoroacetate);

N-[4-(5-oxo-4,5-dihydro-3H-1,4,8b-triazaacenaphthylen-2-yl)benzyl]propan-2-aminium trifluoroacetate;

2-[4-(6-oxo-3,4,5,6-tetrahydro-2H-azepino[5,4,3-cd]indazol-2-yl)benzyl]-2,7-diazoniaspiro[4.5]decane bis(trifluoroacetate);

[4-(8-fluoro-6-oxo-3,4,5,6-tetrahydro-2H-azepino[5,4,3-cd]indazol-2-yl)phenyl]-N,N-dimethylmethanaminium trifluoroacetate;

5-phenyl-3,4-dihydroazepino[3,4,5-hi]indolizin-1(2H)-one;

ethyl 4-(1-oxo-1,2,3,4-tetrahydroazepino[3,4,5-hi]indolizin-5-yl)benzoate;

5-(4-nitrophenyl)-3,4-dihydroazepino[3,4,5-hi]indolizin-1 (2H)-one;
5-[4-(hydroxymethyl)phenyl]-3,4-dihydroazepino[3,4,5-hi] indolizin-1(2H)-one;
N-[4-(1-oxo-1,2,3,4-tetrahydroazepino[3,4,5-hi]indolizin-5-yl)phenyl]nicotinamide;
N-[4-(1-oxo-1,2,3,4-tetrahydroazepino[3,4,5-hi]indolizin-5-yl)phenyl]pyridine-2-carboxamide;
N-[4-(1-oxo-1,2,3,4-tetrahydroazepino[3,4,5-hi]indolizin-5-yl)phenyl]-2-pyrrolidin-1-ylacetamide;
1-methyl-N-[4-(1-oxo-1,2,3,4-tetrahydroazepino[3,4,5-hi] indolizin-5-yl)phenyl]piperidine-4-carboxamide;
3-({[4-(1-oxo-1,2,3,4-tetrahydroazepino[3,4,5-hi]indolizin-5-yl)phenyl]amino}carbonyl)azetidinium chloride;
(3S)-1-methyl-N-[4-(1-oxo-1,2,3,4-tetrahydroazepino[3,4, 5-hi]indolizin-5-yl)phenyl]piperidine-3-carboxamide;
(3R)-1-methyl-N-[4-(1-oxo-1,2,3,4-tetrahydroazepino[3,4, 5-hi]indolizin-5-yl)phenyl]piperidine-3-carboxamide;
(2S)-1-methyl-N-[4-(1-oxo-1,2,3,4-tetrahydroazepino[3,4, 5-hi]indolizin-5-yl)phenyl]piperidine-2-carboxamide;
(2R)-1-methyl-N-[4-(1-oxo-1,2,3,4-tetrahydroazepino[3,4, 5-hi]indolizin-5-yl)phenyl]piperidine-2-carboxamide;
5-{4-[(dimethylamino)methyl]phenyl}-3,4-dihydroazepino [3,4,5-hi]indolizin-1(2H)-one;
5-{4-[(methylamino)methyl]phenyl}-3,4-dihydro azepino [3,4,5-hi]indolizin-1(2H)-one;
5-{4-[(4-methylpiperazin-1-yl)methyl]phenyl}-3,4-dihydroazepino[3,4,5-hi]indolizin-1(2H)-one;
5-{4-[(isopropylamino)methyl]phenyl}-3,4-dihydroazepino [3,4,5-hi]indolizin-1(2H-one;
5-(4-{[(2-hydroxyethyl)amino]methyl}phenyl)-3,4-dihydroazepino[3,4,5-hi]indolizin-1(2H-one;
and pharmaceutically acceptable salts, free bases and tautomers thereof.

Included in the instant invention is the free base of compounds of Formula I, as well as the pharmaceutically acceptable salts and stereoisomers thereof. The compounds of the present invention can be protonated at the N atom(s) of an amine and/or N containing heterocycle moiety to form a salt. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic, organic acid or polymeric acid. For example, conventional non-toxic salts include those derived from inorganic acids such as hydrochloric, hydrobromic, hydroiodic, sulfuric, sulfurous, sulfamic, phosphoric, phosphorous, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, palmitic, gluconic, ascorbic, phenylacetic, aspartic, cinnamic, pyruvic, ethanesulfonic, ethane, disulfonic, valeric, trifluoroacetic and the like. Examples of suitable polymeric salts include those derived from the polymeric acids such as tannic acid, carboxymethyl cellulose. Preferably, a pharmaceutically acceptable salt of this invention contains 1 equivalent of a compound of formula (I) and 1, 2 or 3 equivalent of an inorganic or organic acid. More particularly, pharmaceutically acceptable salts of this invention are the trifluoroacetate or the chloride salts, especially the trifluoroacetate salts.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, lysine, betaine caffeine, choline, $N,N^1$-dibenzylethylenediamine, ethylamine, diethylamine, 2-diethylaminoethanol, 2-dimethylaminoethanol, ethanolamine, diethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine, dicyclohexylamine, butylamine, benzylamine, phenylbenzylamine, tromethamine and the like.

The preparation of the pharmaceutically acceptable salts described above and other typical pharmaceutically acceptable salts is more fully described by Berg et al (1977) *J. Pharm. Sci., 'Pharmaceutical Salts'*, 66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The present invention provides compounds for use in therapy.

The invention provides compounds for use in the treatment or prevention of conditions which can be ameliorated by the inhibition of poly(ADP-ribose)polymerase (PARP) (see, for example, *Nature Review Drug Discovery* (2005) 4:421-440).

Thus, the present invention provides a compound of formula I for use in the manufacture of a medicament for the treatment or prevention of conditions which can be ameliorated by the inhibition of poly(ADP-ribose)polymerase (PARP).

The present invention also provides a method for the treatment or prevention of conditions which can be ameliorated by the inhibition of poly(ADP-ribose)polymerase (PARP), which method comprises administration to a patient in need thereof of an effective amount of a compound of formula I or a composition comprising a compound of formula I.

The PARP inhibitors of the present invention are useful for the treatment of the diseases specified in WO 2005/082368.

PARP inhibitors have been demonstrated as being useful for treatment of inflammation diseases (see *Pharmacological Research* (2005) 52:72-82 and 83-92).

The compounds of the invention are useful for the treatment of inflammatory diseases, including conditions resulting from organ transplant rejection, such as; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, and chronic obstructive airway disease; inflammatory diseases of the eye including corneal dystrophy, trachoma, onchocerciasis, uveitis, sympatheticophthalmitis and endophthalmitis; chronic inflammatory diseases of the gum, including gingivitis and periodontitis; tuberculosis; leprosy; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; diabetic complications, including, but not limited to, immune-complex vasculitis, systemic lupus erythematosus (SLE); inflammatory diseases of the heart such as cardiomyopathy, ischemic heart disease, hypercholesterolemia, and atherosclerosis; as well as various other diseases that can have significant inflammatory components, including preeclampsia, chronic liver failure, brain and spinal cord trauma and multiple organ dysfunction syndrome (MODS) (multiple organ failure (MOP)). The inflammatory disease can also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g. by a chemotherapeutic agent that is administered as a treatment for cancer.

Thus, the present invention provides a compound of formula I for use in the manufacture of a medicament for treating or preventing inflammatory diseases.

The present invention also provides a method for the treatment or prevention of inflammatory diseases, which method comprises administration to a patient in need thereof of an effective amount of a compound of formula I or a composition comprising a compound of formula I.

PARP inhibitors have also been shown to be useful for treating acute and chronic myocardial diseases (see *Pharmacological Research* (2005) 52:34-43). For instance, it has been demonstrated that single injections of PARP inhibitors have reduced the infarct size caused by ischemia and reperfusion of the heart or skeletal muscle in rabbits. In these studies, a single injection of 3-amino-benzamide (10 mg/kg), either one minute before occlusion or one minute before reperfusion, caused similar reductions in infarct size in the heart (32-42%) while 1,5-dihydroxyisoquinoline (1 mg/kg), another PARP inhibitor, reduced infarct size by a comparable degree (38-48%). These results make it reasonable to assume that PARP inhibitors could salvage previously ischemic heart or reperfusion injury of skeletal muscle tissue (*PNAS* (1997) 94:679-683). Similar findings have also been reported in pigs (*Eur. J. Pharmacol.* (1998) 359:143-150 and *Ann. Thorac. Surg.* (2002) 73:575-581) and in dogs (*Shock.* (2004) 21:426-32).

PARP inhibitors have been demonstrated as being useful for treating certain vascular diseases, septic shock, ischemic injury and neurotoxicity (*Biochim. Biophys. Acta* (1989) 1014:1-7; *J. Clin. Invest.* (1997) 100: 723-735). PARP has also been demonstrated to play a role in the pathogenesis of hemorrhagic shock (*PNAS* (2000) 97:10203-10208).

The compounds of the instant invention may also be useful in the treatment or prevention of reperfusion injuries, resulting from naturally occurring episodes and during a surgical procedure, such as intestinal reperfusion injury; myocardial reperfusion injury; reperfusion injury resulting from cardiopulmonary bypass surgery, aortic aneurysm repair surgery, carotid endarterectomy surgery, or hemorrhagic shock; and reoxygenation injury resulting from transplantation of organs such as heart, lung, liver, kidney, pancreas, intestine, and cornea.

Thus, the present invention provides a compound of formula I for use in the manufacture of a medicament for the treatment or prevention of reperfusion injuries.

The present invention also provides a method for the treatment or prevention of reperfusion injuries, which method comprises administration to a patient in need thereof of an effective amount of a compound of formula I or a composition comprising a compound of formula I.

The compounds of the instant invention may also be useful in the treatment or prevention of ischemic conditions, including those resulting from organ transplantation, such as stable angina, unstable angina, myocardial ischemia, hepatic ischemia, mesenteric artery ischemia, intestinal ischemia, critical limb ischemia, chronic critical limb ischemia, cerebral ischemia, acute cardiac ischemia, ischemia kidney disease, ischemic liver disease, ischemic retinal disorder, septic shock, and an ischemic disease of the central nervous system, such as stroke or cerebral ischemia.

Thus, the present invention provides a compound of formula I for use in the manufacture of a medicament for the treatment or prevention of ischemic conditions.

The present invention also provides a method for the treatment or prevention of ischemic conditions, which method comprises administration to a patient in need thereof of an effective amount of a compound of formula I or a composition comprising a compound of formula I.

The present invention provides a compound of formula I for use in the manufacture of a medicament for the treatment or prevention of stroke.

The present invention also provides a method for the treatment or prevention of stroke, which method comprises administration to a patient in need thereof of an effective amount of a compound of formula I or a composition comprising a compound of formula I.

The compounds of the instant invention may also be useful for the treatment or prevention of chronic or acute renal failure.

Thus, the present invention provides a compound of formula I for use in the manufacture of a medicament for the treatment or prevention of renal failure.

The present invention also provides a method for the treatment or prevention of renal failure, which method comprises administration to a patient in need thereof of an effective amount of a compound of formula I or a composition comprising a compound of formula I.

The compounds of the instant invention may also be useful for the treatment or prevention of vascular diseases other than cardiovascular diseases, such as peripheral arterial occlusion, thromboangitis obliterans, Reynaud's disease and phenomenon, acrocyanosis, erythromelalgia, venous thrombosis, varicose veins, arteriovenous fistula, lymphedema and lipedema.

Thus, the present invention provides a compound of formula I for use in the manufacture of a medicament for the treatment or prevention of vascular diseases other than cardiovascular diseases.

The present invention also provides a method for the treatment or prevention of vascular diseases other than cardiovascular diseases, which method comprises administration to a patient in need thereof of an effective amount of a compound of formula I or a composition comprising a compound of formula I.

The compounds of the instant invention may also be useful for the treatment or prevention of cardiovascular diseases such as chronic heart failure, atherosclerosis, congestive heart failure, circulatory shock, cardiomyopathy, cardiac transplant, myocardialinfarction, and a cardiac arrhythmia, such as atrial fibrillation, supraventricular tachycardia, atrial flutter, and paroxysmal atrial tachycardia.

Thus, the present invention provides a compound of formula I for use in the manufacture of a medicament for the treatment or prevention of cardiovascular diseases.

The present invention also provides a method for the treatment or prevention of cardiovascular diseases, which method comprises administration to a patient in need thereof of an effective amount of a compound of formula I or a composition comprising a compound of formula I.

In vitro and in vivo experiments have demonstrated that PARP inhibitors can be used for the treatment or prevention of autoimmune diseases such as Type I diabetes and diabetic complications (*Pharmacological Research* (2005) 52:60-71).

The compounds of this invention may also be useful for the treatment and prevention of diabetes mellitus, including Type I diabetes (Insulin Dependent Diabetes Mellitus), Type II diabetes (Non-Insulin Dependent Diabetes Mellitus), gestational diabetes, autoimmune diabetes, insulinopathies, diabetes due to pancreatic disease, diabetes associated with other endocrine diseases (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by (3-cell toxins. The compounds of this invention may also be useful for the treatment or prevention of diabetic complications, such as diabetic cataract, glaucoma, retinopathy, nephropathy, (such asmicroaluminuria and progressive diabetic nephropathy), polyneuropathy, gangrene of the feet, atherosclerotic coronary arterial disease, peripheral arterial disease, nonketotic hyperglycemic-hyperosmolar coma, mononeuropathies, autonomic neuropathy, foot ulcers, joint problems, and a skin or mucous membrane complication (such as an infection, a shin spot, a candidal infection or necrobiosis lipoidica diabeticorumobesity), hyperlipidemia, hypertension, syndrome of insulin resistance, coronary artery disease, retinopathy, diabetic neuropathy, polyneuropathy, mononeuropathies, autonomic neuropathy, a foot ulcer, a joint problem, a fungal infection, a bacterial infection, and cardiomyopathy.

Thus, the present invention provides a compound of formula I for use in the manufacture of a medicament for the treatment or prevention of diabetes.

The present invention also provides a method for the treatment or prevention of diabetes, which method comprises administration to a patient in need thereof of an effective amount of a compound of formula I or a composition comprising a compound of formula I.

The compounds of this invention may also be useful for the treatment or prevention of cancer including solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, skin cancer, melanoma, neuroblastoma and retinoblastoma; blood-borne cancers such as acute lymphoblastic leukemia ("ALL"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlyniphocyctic leukemia, acute undifferentiated leukemia, chronic myelocytic leukemia ("CML"), chronic lymphocytic leukemia ("CLL"), hairy cell leukemia and multiple myeloma; acute and chronic leukemias such as lymphoblastic, myelogenous, lymphocytic, myelocytic leukemias; Lymphomas such as Hodgkin's disease, non-Hodgkin's Lymphoma, Multiple myeloma, Waldenstrom's macroglobulinemia, Heavy chain disease and Polycythemia vera; CNS and brain cancers such as glioma, pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain tumor, meningioma, spinal tumor and medulloblastoma.

Thus, the present invention provides a compound of formula I for use in the manufacture of a medicament for the treatment or prevention of cancer.

The present invention also provides a method for the treatment or prevention of cancer, which method comprises administration to a patient in need thereof of an effective amount of a compound of formula I or a composition comprising a compound of formula I.

The compounds of the present invention may also be used for the treatment of cancer which is deficient in Homologous Recombination (HR) dependent DNA DSB repair activity (see WO 2006/021801).

The HR dependent DNA DSB repair pathway repairs double-strand breaks (DSBs) in DNA via homologous mechanisms to reform a continuous DNA helix (*Nat. Genet.* (2001) 27(3):247-254). The components of the HR dependent DNA DSB repair pathway include, but are not limited to, ATM (NM-000051), RAD51 (NM-002875), RAD51 L1 (NM-002877), RAD51C (NM-002876), RAD51L3 (NM-002878), DMC1 (NM-007068), XRCC2 (NM7005431), XRCC3 (NM-005432), RAD52 (NM-002879), RAD54L (NM-003579), RAD54B (NM-012415), BRCA-1 (NM-007295), BRCA-2 (NM-000059), RAD5O (NM-005732), MREI 1A (NM-005590), NB51, (NM-002485), ADPRT (PARP-1), ADPRTL2 (PARP-2), CTPS, RPA, RPA1, RPA2, RPA3, XPD, ERCC1, XPF, MMS19, RAD51p, RAD51D,DMC1, XRCCR, RAD50, MRE11, NB51, WRN, BLMKU70, RU80, ATRCHK1, CHK2, FANCA, FANCB, FANCC, FANCD1, FANCD2, FANCE, FANCF, FANCG, RAD1 and RAD9. Other proteins involved in the HR dependent DNA DSB repair pathway include regulatory factors such as EMSY (*Cell* (2003) 115:523-535).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterized in the art (see for example, *Science* (2001) 291: 1284-1289) and include the components listed above.

The present invention provides a compound of formula I for use in the manufacture of a medicament for the treatment or prevention of a cancer which is deficient in HR dependent DNA DSB repair activity.

The present invention also provides a method for the treatment or prevention of a cancer which is deficient in HR dependent DNA DSB repair activity, which method comprises administration to a patient in need thereof of an effective amount of a compound of formula I or a composition comprising a compound of formula I In an embodiment the cancer cells are deficient in the HR dependent DNA DSB repair activity of one or more phenotypes selected from ATM (NM-000051), RAD51 (NM-002875), RAD51 L1 (NM-002877), RAD51C (NM-002876), RAD51L3 (NM-002878), DMC1 (NM-007068), XRCC2 (NM7005431), XRCC3 (NM-005432), RAD52 (NM-002879), RAD54L (NM-003579), RAD54B (NM-012415), BRCA-1 (NM-007295), BRCA-2 (NM-000059), RAD50 (NM-005732), MREI 1A (NM-005590), NBS1 (NM-002485), ADPRT (PARP-1), ADPRTL2 (PARP-2), CTPS, RPA, RPA1, RPA2, RPA3, XPD, ERCC1, XPF, MMS19, RAD51p, RAD51D,DMC1, XRCCR, RAD50, MRE11, NB51, WRN, BLMKU70, RU80, ATRCHK1, CHK2, FANCA, FANCB, FANCC, FANCD1, FANCD2, FANCE, FANCF, FANCG, RAD1 and RAD9.

In another embodiment, the cancer cells have a BRCA1 and/or a BRCA2 deficient phenotype. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (*Cell* (2003) 115:523-535).

BRCA-1 and BRCA-2 are known tumor suppressors whose wild-type alleles are frequently lost in tumors of heterozygous carriers (*Oncogene*, (2002) 21(58):8981-93; *Trends Mol Med.*, (2002) 8(12):571-6). The association of BRCA-1 and/or BRCA-2 mutations with breast cancer has been well-characterized (*Exp Clin Cancer Res.*, (2002) 21 (3 Suppl):9-12). Amplification of the EMSY gene, which encodes a BRCA-2 binding factor, is also known to be associated with breast and ovarian cancer. Carriers of mutations in BRCA-1 and/or BRCA-2 are also at elevated risk of cancer of the ovary, prostate and pancreas. The detection of variation in BRCA-1 and BRCA-2 is well-known in the art and is described, for example in EP 699 754, EP 705 903, *Genet. Test* (1992) 1:75-83; *Cancer Treat Res* (2002) 107:29-59; *Neoplasm* (2003) 50(4):246-50; *Ceska Gynekol* (2003) 68(1): 11-16). Determination of amplification of the BRCA-2 binding factor EMSY is described in *Cell* 115:523-535. PARP inhibitors have been demonstrated as being useful for the specific killing of BRCA-1 and BRCA-2 deficient tumors (*Nature* (2005) 434:913-916 and 917-921; and *Cancer Biology & Therapy* (2005) 4:934-936).

Thus, the present invention provides a compound of formula I for use in the manufacture of a medicament for the treatment or prevention of BRCA-1 or BRCA-2 deficient tumors.

The present invention also provides a method for the treatment or prevention of BRCA-1 or BRCA-2 deficient tumors, which method comprises administration to a patient in need thereof of an effective amount of a compound of formula I or a composition comprising a compound of formula I.

In an embodiment, the PARP inhibitors of the present can be used in prophylactic therapy for elimination of BRCA2-deficient cells (see, *Cancer Res*. (2005) 65:10145).

The compounds of this invention may be useful for the treatment or prevention of neurodegenerative diseases, including, polyglutamine-expansion-related neurodegeneration, Huntington's disease, Kennedy's disease, spinocerebellar ataxia, dentatorubral-pallidoluysian atrophy (DRPLA), protein-aggregation-related neurodegeneration, Machado-Joseph's disease, Alzheimer's disease, Parkinson's disease, amyotrophic lateral sclerosis, spongiform encephalopathy, a prion-related disease and multiple sclerosis (MS).

Thus, the present invention provides a compound of formula I for use in the manufacture of a medicament for treating or preventing neurodegenerative diseases.

The present invention also provides a method for treating or preventing neurodegenerative diseases, which method comprises administration to a patient in need thereof of an effective amount of a compound of formula I or a composition comprising a compound of formula I.

The compounds of the present invention may also be useful for the treatment or prevention of retroviral infection (U.S. Pat. No. 5,652,260 and *J. Virology*, (1996) 70(6):3992-4000), retinal damage (*Curr. Eye Res*. (2004), 29:403), skin senescence and UV-induced skin damage (U.S. Pat. No. 5,589,483 and *Biochem. Pharmacol* (2002) 63:921). It has also been demonstrated that efficient retroviral infection of mammalian cells is blocked by the inhibition of PARP activity. Such inhibition of recombinant retroviral vector infections has been shown to occur in various different cell types).

The compounds of the invention are useful for the treatment or prevention of premature aging and postponing the onset of age-related cellular dysfunction (*Biochem. Biophys. Res. Comm*. (1994) 201(2): 665-672 and *Pharmacological Research* (2005) 52:93-99).

The compounds of this invention may be administered to mammals, preferably humans, either alone or in combination with pharmaceutically acceptable carriers, excipients, diluents, adjuvants, fillers, buffers, stabilisers, preservatives, lubricants, in a pharmaceutical composition, according to standard pharmaceutical practice.

The compounds of this invention may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, (e.g. by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal); and by implant of a depot (e.g. subcutaneously or intramuscularly).

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a subject, the selected dosage level will depend on a variety of factors including, but not limited to, the activity of the particular compound, the severity of the individuals symptoms, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

The instant compounds are also useful in combination with anti-cancer agents or chemotherapeutic agents.

PARP inhibitors have been shown to enhance the efficacy of anticancer drugs (*Pharmacological Research* (2005) 52:25-33), including platinum compounds such as cisplatin and carboplatin (*Cancer Chemother Pharmacol* (1993) 33:157-162 and *Mol Cancer Ther* (2003) 2:371-382). PARP inhibitors have been shown to increase the antitumor activity of topoisomerase I inhibitors such as Irinotecan and Topotecan (*Mol Cancer Ther* (2003) 2:371-382; and *Clin Cancer Res* (2000) 6:2860-2867) and this has been demonstrated in in vivo models (*J Natl Cancer Inst* (2004) 96:56-67).

PARP inhibitors have been shown to act as radiation sensitizers. PARP inhibitors have been reported to be effective in radiosensitizing (hypoxic) tumor cells and effective in preventing tumor cells from recovering from potentially lethal (*Br. J. Cancer* (1984) 49(Suppl. VI):34-42; and *Int. J. Radiat. Biol.* (1999) 75:91-100) and sub-lethal (*Clin. Oncol.* (2004) 16(1):29-39) damage of DNA after radiation therapy, presumably by their ability to prevent DNA strand break rejoining and by affecting several DNA damage signaling pathways.

The compounds of this invention may be useful as chemo- and radiosensitizers for cancer treatment. They are useful for the treatment of mammals who have previously undergone or are presently undergoing treatment for cancer. Such previous treatments include prior chemotherapy, radiation therapy, surgery or immunotherapy, such as cancer vaccines.

Thus, the present invention provides a combination of a compound of formula I and an anti-cancer agent for simultaneous, separate or sequential administration.

The present invention also provides a compound of formula I for use in the manufacture of a medicament for use as an adjunct in cancer therapy or for potentiating tumor cells for treatment with ionizing radiation or chemotherapeutic agents.

The present invention also provides a method of chemotherapy or radiotherapy, which method comprises administration to a patient in need thereof of an effective amount of a compound of formula I or a composition comprising a compound of formula I in combination with ionizing radiation or chemotherapeutic agents.

In combination therapy, the compounds of this invention can be administered prior to (e.g., 5 minutes, 15 minutes, 30 minutes, 45 minutes, 1 hour, 2 hours, 4 hours, 6 hours, 12 hours, 24 hours, 48, hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anticancer agent to a subject in need thereof. In various embodiments the instant compounds and another anticancer agent are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart.

The compounds of this invention and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

Examples of cancer agents or chemotherapeutic agents for use in combination with the compounds of the present invention can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors, HIV protease inhibitors, reverse transcriptase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

Examples of "HDAC inhibitors" include suberoylanilide hydroxamic acid (SAHA), LAQ824, LBH589, PXD101, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites, biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, cyclophosphamide, chlorambucil carmustine (BCNU), lomustine (CCNU), busulfan, treosulfan, sertenef, cachectin, ifosfamide, tasonermin, lonidamine, carboplatin, altretamine, prednimustine, dibromodulcitol, ranimustine, fotemustine, nedaplatin, aroplatin, oxaliplatin, temozolomide, methyl methanesulfonate, procarbazine, dacarbazine, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, doxorubicin, epirubicin, pirarubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulphonyl-daunorubicin (see WO 00/50032).

In an embodiment the compounds of this invention can be used in combination with alkylating agents.

Examples of alkylating agents include but are not limited to, nitrogen mustards: cyclophosphamide, ifosfamide, trofosfamide and chlorambucil; nitrosoureas: carmustine (BCNU) and lomustine (CCNU); alkylsulphonates: busulfan and treosulfan; triazenes: dacarbazine, procarbazine and temozolomide; platinum containing complexes: cisplatin, carboplatin, aroplatin and oxaliplatin.

In an embodiment, the alkylating agent is dacarbazine. Dacarbazine can be administered to a subject at dosages ranging from about 150 mg/m2 (of a subject's body surface area) to about 250 mg/m2. In another embodiment, dacarbazine is administered intravenously to a subject once per day for five consecutive days at a dose ranging from about 150 mg/m2 to about 250 mg/m2.

In an embodiment, the alkylating agent is procarbazine. Procarbazine can be administered to a subject at dosages ranging from about 50 mg/m2 (of a subject's body surface area) to about 100 mg/m2. In another embodiment, procarbazine is administered intravenously to a subject once per day for five consecutive days at a dose ranging from about 50 mg/m2 to about 100 mg/m2.

PARP inhibitors have been shown to restore susceptibility to the cytotoxic and antiproliferative effects of temozolomide (TMZ) (see *Curr Med Chem* (2002) 9:1285-1301 and *Med Chem Rev Online* (2004) 1:144-150). This has been demonstrated in a number of in vitro models (*Br J Cancer* (1995) 72:849-856; *Br J Cancer* (1996) 74:1030-1036; *Mol Pharmacol* (1997) 52:249-258; *Leukemia* (1999) 13:901-909; *Glia* (2002) 40:44-54; and *Clin Cancer Res* (2000) 6:2860-2867 and (2004) 10:881-889) and in vivo models (*Blood* (2002) 99:2241-2244; *Clin Cancer Res* (2003) 9:5370-5379 and *J Natl Cancer Inst* (2004) 96:56-67).

In an embodiment, the alkylating agent is temozoloamide. Temozolomide can be administered to a subject at dosages ranging from about 150 mg/m2 (of a subject's body surface area) to about 200 mg/m2. In another embodiment, temozolomide is administered orally to an animal once per day for five consecutive days at a dose ranging from about 150 mg/m2 to about 200 mg/m2.

Examples of anti-mitotic agents include: allocolchicine, halichondrin B, colchicine, colchicine derivative, dolstatin 10, maytansine, rhizoxin, thiocolchicine and trityl cysteine.

An example of a hypoxia activatable compound is tirapazamine.

Examples of proteasome inhibitors include but are not limited to lactacystin, bortezomib, epoxomicin and peptide aldehydes such as MG 132, MG 115 and PSI.

Examples of microtubule inhibitors/microtubule-stabilising agents include paclitaxel, vindesine sulfate, vincristine, vinblastine, vinorelbine, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-proplyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, exatecan, gimetecan, diflomotecan, silyl-camptothecins, 9-aminocamptothecin, camptothecin, crisnatol, mitomycin C, 6-ethoxypropionyl-3', 4'-O-exo-benzylidene-chartreusin, 9-methoxy-N,N-dimethyl-5-nitropyrazolo[3,4,5-k1]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1, 2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa, 9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3'4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna; non-camptothecin topoisomerase-1 inhibitors such as indolocarbazoles; and dual topoisomerase-1 and II inhibitors such as benzophenazines, XR 20 115761MLN 576 and benzopyridoindoles.

In an embodiment, the topoisomerase inhibitor is irinotecan. Irinotecan can be administered to a subject at dosages ranging from about 50 mg/m2 (of a subject's body surface area) to about 150 mg/m2. In another embodiment, irinotecan is administered intravenously to a subject once per day for five consecutive days at a dose ranging from about 50 mg/m2 to about 150 mg/m2 on days 1-5, then again intravenously once per day for five consecutive days on days 28-32 at a dose ranging from about 50 mg/m2 to about 150 mg/m2, then again intravenously once per day for five consecutive days on days 55-59 at a dose ranging from about 50 mg/m2 to about 150 mg/m2.

Examples of inhibitors of mitotic kinesins, and in particular the human mitotic kinesin KSP, are described in PCT Publications WO 01/30768, WO 01/98278, WO 02/056880, WO 03/050,064, WO 03/050,122, WO 03/049,527, WO 03/049,679, WO 03/049,678, WO 03/039460, WO 03/079973, WO 03/099211, WO 2004/039774, WO 03/105855, WO 03/106417, WO 2004/087050, WO 2004/058700, WO 2004/058148 and WO 2004/037171 and US applications US 2004/132830 and US 2004/132719. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as 03139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(5)-ethyl]-2, 5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer* (1999), 35(9):1394-1401.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-$\alpha$, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (*PNAS* (1992) 89:7384; *JNCI* (1982) 69:475; *Arch. Opthalmol.* (1990) 108:573; *Anat. Rec.* (1994) 238:68; *FEBS Letters* (1995) 372:83; *Clin, Orthop.* (1995) 313:76; *J. Mol. Endocrinol.* (1996) 16:107; *Jpn. J. Pharmacol.* (1997) 75:105; *Cancer Res.* (1997) 57:1625 (1997); *Cell* (1998) 93:705; *Intl. J. Mol. Med.* (1998) 2:715; *J. Biol. Chem.* (1999) 274:9116)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see *J. Lab. Clin. Med.* (1985) 105:141-145), and antibodies to VEGF (see *Nature Biotechnology* (1999) 17:963-968; Kim et al (1993) *Nature* 362:841-844; WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* (2000) 38:679-692). Examples of such agents that modulate or inhibit the coagulation and fibrinolysis pathways include, but are not limited to, heparin (see *Thromb. Haemost.* (1998) 80:10-23), low molecular weight heparins and carboxypeptidase U inhibitors (also known as inhibitors of active thrombin activatable fibrinolysis inhibitor [TAFIa]) (see *Thrombosis Res.* (2001) 101:329-354). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, staurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR (for example those disclosed in WO 03/059951), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598, all of which are hereby incorporated by reference.

Inhibitors of COX-2 that are particularly useful in the instant method of treatment are 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 35$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\beta_5\alpha_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\beta_5\alpha_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-k1]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

PAPR inhibitors have also been shown to prevent the appearance of necrosis induced by selective N3-adenine methylating agents such as $MeOSO_2(CH_2)$-lexitropsin (Me-Lex) (*Pharmacological Research* (2005) 52:25-33).

In an embodiment, the compounds of the present invention are useful for the treatment or prevention of the appearance of necrosis induced by selective N3-adenine methylating agents such as $MeOSO_2(CH_2)$-lexitropsin (Me-Lex).

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* (1998) 31:909-913; *J. Biol. Chem.* (1999) 274: 9116-9121; *Invest. Ophthalmol. Vis. Sci.* (2000) 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* (2001) 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697).

Another embodiment of the instant invention is the use of the presently disclosed compounds in combination with antiviral agents (such as nucleoside analogs including ganciclovir for the treatment of cancer. See WO 98/04290.

Another embodiment of the instant invention is the use of the presently disclosed compounds in combination with gene therapy for the treatment of cancer. For an overview of genetic strategies to treating cancer see Hall et al (*Am J Hum Genet* (1997) 61:785-789) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p 53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August (1998) 5(8):1105-13), and interferon gamma (*J Immunol* (2000) 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853, verapamil and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, $GABA_B$ receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa)

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

Thus, the scope of the instant invention encompasses the use of the instantly claimed compounds in combination with ionizing radiation and/or in combination with a second compound selected from: HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treatment" refers to the treatment of a mammal afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The term "adjunct" refers to the use of compounds in conjunction with known therapeutic means. Such means include cytotoxic regimes of drugs and/or ionising radiation as used in the treatment of different cancer types. In particular, the active compounds are known to potentiate the actions of a number of cancer chemotherapy treatments, which include the topoisomerase class of poisons (e.g. topotecan, irinotecan, rubitecan), most of the known alkylating agents (e.g. DTIC, temozolamide) and platinum based drugs (e.g. carboplatin, cisplatin) used in treating cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MN/IP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: HDAC inhibitors, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of cell proliferation and survival signaling, an agent that interfers with a cell cycle checkpoint, an apoptosis inducing agent and a bisphosphonate.

These and other aspects of the invention will be apparent from the teachings contained herein.

The compounds of this invention were prepared according to the following procedures. All variables within the formulae are as defined above.

Abbreviations Used in the Description of the Chemistry and in the Examples that Follow are:

AcOH: acetic acid; DCE: dicholoroethane; DCM: dichloromethane; DMF: dimethylforamide; DMSO: dimethylsulfoxide; EtOH: ethanol; EtOAc: ethyl acetate; i-PrOH: 2-propanol; MeCN: acetonitrile; MeOH: methanol; THF: tetrahydrofuran; Et$_2$O: diethyl ether; TFA: trifluoracetic acid; TIPS: triisopropylsilane; DIBAL-H: diisobutylaluminoium hydride; NaHMDS: sodium bis(trimethylsilyl)amide; dppf: 1,1'-bis[diphenylphosphine]ferrocene; TBDMSOTf: tert-butyldimethylsilyl trifluoromethanesulfonate; TBAF: tetrabutylammonium fluoride; (Boc)$_2$O; di-tert-butyl dicarbonate; HATU: 0-(7-azabenzotriazol-1-yl-N,N,N',N'-tetramethyluronium hexafluorophosphate; DIEA: N,N-diisopropylethylamine; eq.: equivalent(s); sat. aq.: saturated aqueous; RT: room temperature; min: minutes; h: hour(s); M: molar; wt: weight; atm: atmosphere; NMR: nuclear magnetic resonance; MS: mass spectrometry; ES: electrospray; RP-HPLC: reversed phase high-pressure liquid chromatography; SCX: cationic exchange resin; $^t$BuOH: tert-butanol; Xphos: 2-dicyclohexylphosphino-2',4'6'-triisopropylbiphenyl; and TEA: triethylamine.

Compounds of formula I wherein b is 2 and each of R$^1$ and R$^2$ is hydrogen can be prepared by hydrolysis of a compound of formula IA, followed by reductive amination with a protected ammonia derivative:

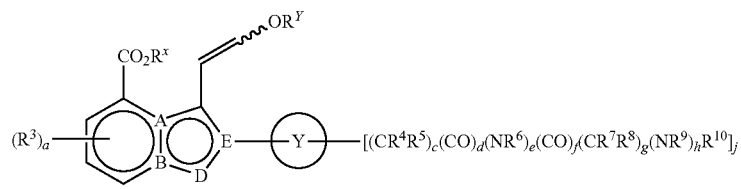

(IA)

wherein a, c, d, e, f, g, h, j, A, B, D, E, R$^3$, R$^4$, R$^5$, R$^6$, R$^7$, R$^8$, R$^9$, R$^{10}$ and Y are as defined above, R$^x$ is C$_{1-6}$alkyl and R$^y$ is C$_{1-6}$alkyl, for example ethyl.

The hydrolysis is generally carried out using a hydrolysis agent such as Hg(AcO)$_2$, in solvents such as THF and water at about RT to 50° C.

The reductive amination can generally be carried out using ammonia substituted by a protecting group such as 2,4-dimethoxybenzyl, in the presence of a reducing agent such as NaBH$_3$CN, in a solvent such as MeOH at about RT. If necessary, a base such as K$_2$CO$_3$ can also be used for the cyclisation step, generally in a solvent such as MeOH at about 120° C. The protecting group can subsequently be removed using standard methods. For example, the deprotection reaction can be carried out using solvents such as TFA, water and TIPS at about 120° C.

Compounds of formula IA can be prepared by bromination of a compound of formula IB, followed by Stille coupling with an alkoxyvinylstannane:

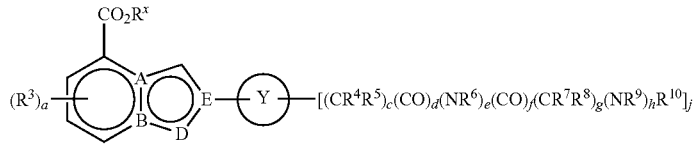

(IB)

wherein a, c, d, e, f, g, h, j, A, B, D, E, R$^3$, R$^4$, R$^5$, R$^6$, R$^7$, R$^8$, R$^9$, R$^{10}$, Y and R$^x$ are as defined above.

The bromination reaction can generally be carried out using Br$_2$ in solvents such as AcOH and DCM at about room temperature. The Stille coupling can be carried out using tributyl[(Z)-2-ethoxyvinyl]stannane, generally in the presence of catalysts such as tris(dibenzenzylideneacetone)dipalladium(0) and tri-t-butylphosphonium tetrafluoroborate, a base such as Cs$_2$CO$_3$, in a solvent such as DMF at about 70° C.

Compounds of formula TB wherein A and D are N, and B and E are C can be prepared by reacting a compound of formula IC with a compound of formula ID:

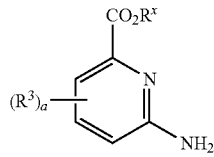

(IC)

(ID)

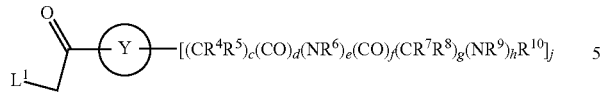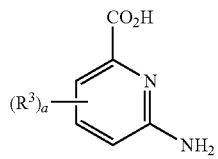

wherein a, c, d, e, f, g, h, j, $R^3$, $R^4$, $R^5$, $R^6$, $R^7$, $R^8$, $R^9$, $R^{10}$, Y and Fe are as defined above and $L^1$ is a leaving group such as halogen, for example bromine. The reaction is generally carried out in the presence of a base such as $NaHCO_3$ and in a solvent such as iPrOH at reflux.

Compounds of formula IC can be prepared by esterification of a compound of formula IE:

(IE)

wherein a and $R^3$ are as defined above. The reaction can be carried out using $R^xOH$, generally in the presence of an acid such as $H_2SO_4$ and in a solvent such as MeOH at reflux.

Compounds of formula I wherein b is 1 and each of $R^1$ and $R^2$ is hydrogen can be prepared by reductive amination of a compound of formula IF with a primary amine:

(IF)

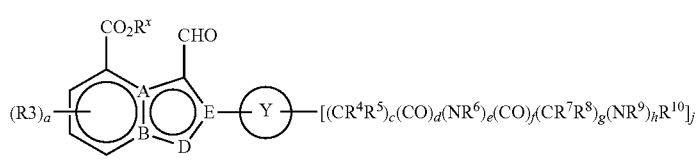

wherein a, c, d, e, f, g, h, j, A, B, D, E, $R^3$, $R^4$, $R^5$, $R^6$, $R^7$, $R^8$, $R^9$, $R^{10}$, Y and $R^x$ are as defined above.

The reductive amination can generally be carried out using ammonia substituted by a protecting group such as 2,4-dimethoxybenzyl, in the presence of a reducing agent such as $NaBH_3CN$, a dehydrating reagent such as $Ti(^iPrO)_4$ and a solvent such as MeOH at about room temperature. The protecting group can subsequently be removed using standard methods, for example those described above for the synthesis of compounds of formula IA.

Compounds of formula IF can be prepared by formylation of a compound of formula IB, generally in the presence of DMF and a chlorinating agent such as $POCl_3$ at reflux.

Compounds of formula IB can alternatively be prepared by sequential oxidation and esterification of a compound of formula IG:

(IG)

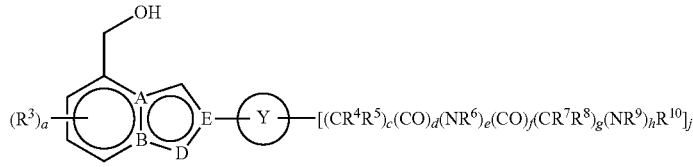

wherein a, c, d, e, f, g, h, j, A, B, D, E, $R^3$, $R^4$, $R^5$, $R^6$, $R^7$, $R^8$, $R^9$, $R^{10}$ and Y are as defined above.

The oxidation can be carried out by firstly using standard oxidising agents, such as $MnO_2$ to produce the aldehyde and then adding $NaH_2PO_4$ and $NaClO_2$ to produce the acid, generally in solvents such as DCM, THF, $H_2O$ and/or $^tBuOH$, at about room temperature. The esterification can be carried out using WO, wherein $L^2$ is a leaving group such as halogen, for example bromine or iodine, generally in the presence of a base such as $Cs_2CO_3$, a solvent such as DMF at about room temperature.

Compounds of formula IG wherein A and B are C; and E and D are N can be prepared by cyclizaton of a compound of formula IH, followed by removal of the protecting group:

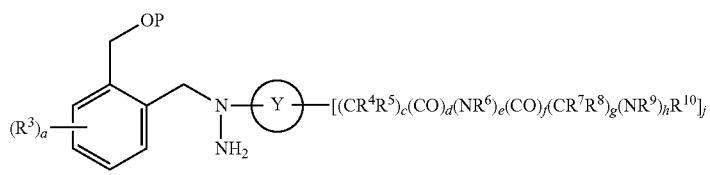
(IH)

wherein a, c, d, e, f, g, h, j, $R^3$, $R^4$, $R^5$, $R^6$, $R^7$, $R^8$, $R^9$, $R^{10}$ and Y are as defined above. The reaction is generally carried out in the presence of dppf, a catalyst such as $Pd(OAc)_2$, a base such as $KO^tBu$ or $NaO^tBu$, at about 80° C.

The protecting group P can be removed by standard conditions, such as by using TBAF, generally in a solvent such as THF at about room temperature.

Compounds of formula IH can be prepared by reacting a compound of formula IJ with a compound of formula IK:

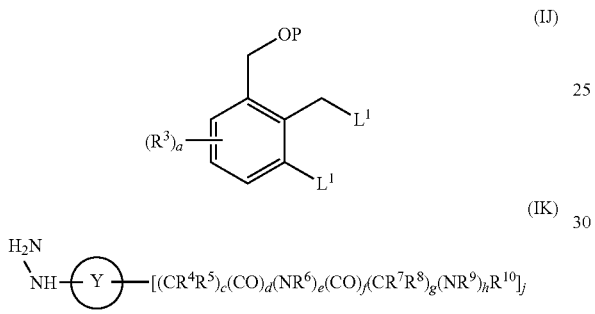
(IJ)

(IK)

wherein a, c, d, e, f, g, h, j, $R^3$, $R^4$, $R^5$, $R^6$, $R^7$, $R^8$, $R^9$, $R^{10}$ and Y are as defined above and each $L^1$ is independently as defined above. The reaction is generally carried out in the presence of NaHMDS, in a solvent such as THF at about 0° C. to room temperature.

Compounds of formula I wherein A and E are CH, D is C and B is N can be prepared by reacting a compound of formula ID with a compound of formula IL:

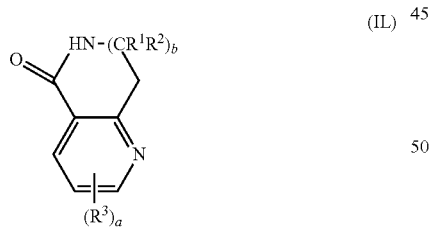
(IL)

wherein a and $R^3$ are as defined above. The reaction is generally carried out by firstly refluxing the reagents in a solvent such as MeOH for about 24 hours and then adding a base such as MeONa and a solvent such as toluene and refluxing the reaction mixture.

Compounds of formula IL wherein each of $R^1$ and $R^2$ is hydrogen can be prepared by hydrogenation and subsequent cyclization of a compound of formula IM:

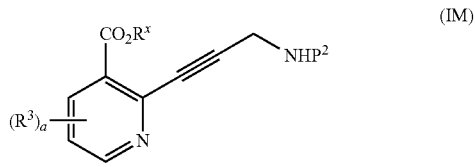
(IM)

wherein $R^x$ is as defined above and $P^2$ is a protecting group such as carbonylbenzyl. The hydrogenation and cyclization can generally be carried out under a hydrogen atmosphere, in the presence of a catalyst such as Pd on carbon, in a solvent such as MeOH at about room temperature.

Compounds of formula I can alternatively be prepared by cyclization of a compound of formula IN:

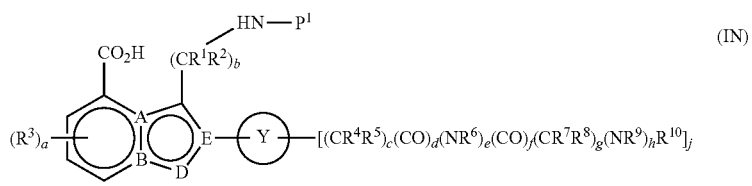
(IN)

wherein a, c, d, e, f, g, h, j, $R^1$, $R^2$, $R^3$, $R^4$, $R^5$, $R^6$, $R^7$, $R^8$, $R^9$, $R^{10}$ and Y are as defined above and $P^1$ is a protecting group such as 2,4-dimethoxybenzyl. The reaction can generally be carried out in the presence of cyclization agents such as HATU and DIEA in a solvent such as DMF at about room temperature.

Where the synthesis of intermediates and starting materials is not described, these compounds are commercially available or can be made from commercially available compounds by standard methods or by extension of the Examples herein.

Compounds of formula I may be converted to other compounds of formula I by known methods or by methods described in the Examples.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis*, 3rd Edition, Greene, T. W. and Wuts, P. G. M.; Wiley Interscience, 1999 and Kocienski, P. J. *Protecting Groups*, Thieme, 1994. The protecting groups may be removed at a convenient subsequent stage using methods known from the art. For example, when the Boc protecting group is present, it may be removed by the addition of TFA in solvents such as DCM and/or MeCN at about room temperature. EtOAc in the presence of HCl and 1,4-dioxane may alternatively be used, at about room temperature. The benzylcarbonyl protecting group can be removed by hydrogenation using standard methods, such as treating with a catalyst such as Pd/C, in a solvent such as methanol under a hydrogen atmosphere.

The compounds of this invention were prepared according to the following schemes. All variables within the formulae are as defined above.

Scheme 1

A procedure to synthesize derivatives of compounds of formula I wherein A and D are N, and B and E are CH is shown in scheme 1. Following initial conversion of the starting 6-aminopyridine-2-carboxylic acid into the corresponding ester, reaction with an α-bromoacetophenone led to the formation of a 2-arylimidazo[1,2-α]pyridine ring. Selective bromination in position 3 using $Br_2$ in AcOH was followed by Stille coupling with using $Pd_2(dba)_3/P(^tBu)_3BF_4$ as catalityc system. The 7-membered ring lactam was formed by hydrolysis of the enolether using a reagents such as $Hg(AcO)_2$ in $THF/H_2O$ at 40° C. followed by reductive amination with the appropriate primary amine in the presence of $NaBH_3CN$ and in situ cyclization. Finally, deprotection of the amide group gives the desired inhibitors.

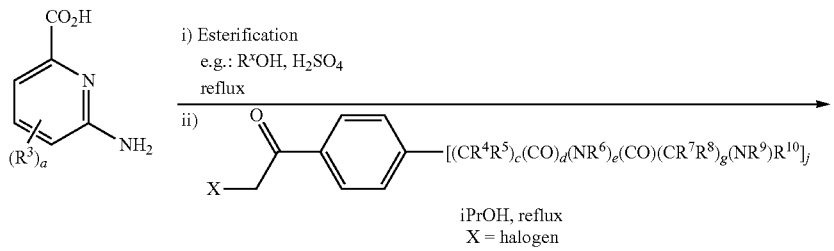

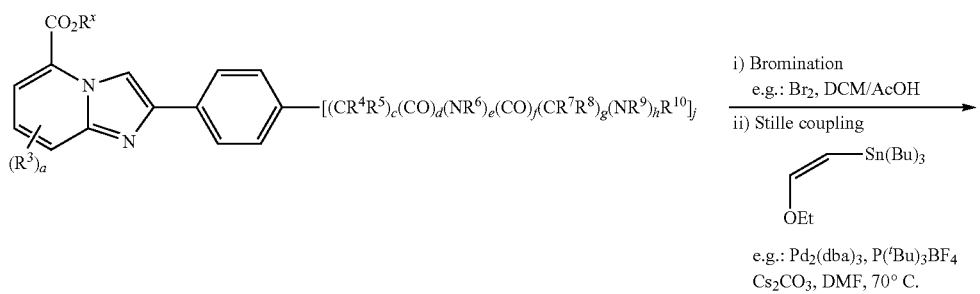

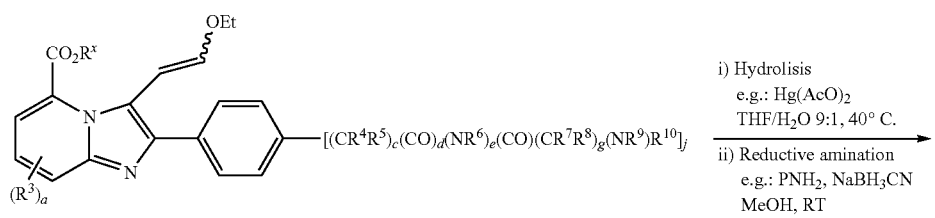

-continued

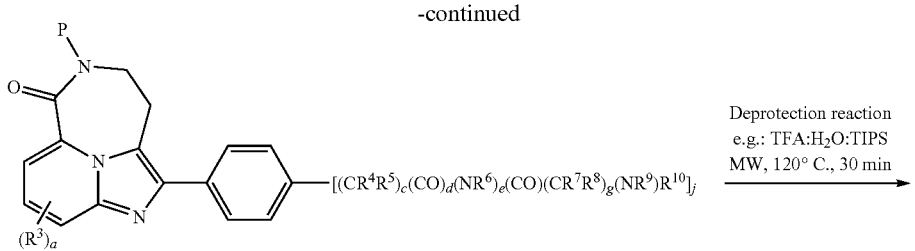

Deprotection reaction
e.g.: TFA:H₂O:TIPS
MW, 120° C., 30 min

P = Protecting group

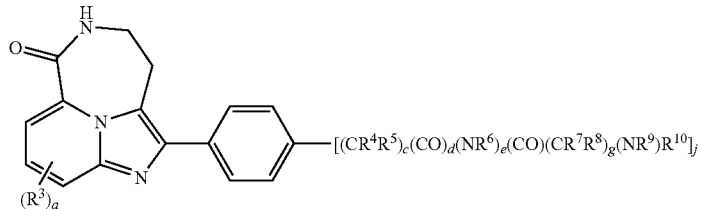

Scheme 2
A different tricyclic scaffold can be prepared from the 2-arylimidazo[1,2-α]pyridine intermediate as described in scheme 2. Treatment of the imidazo[1,2-α]pyridine with POCl₃ in DMF led to the introduction of a carbaldehyde group in position 3. Reductive amination with the appropriate primary amine in the presence of NaBH₃CN and using Ti($^i$PrO)₄ as Lewis acid led to the corresponding secondary amine that in situ cyclised to form the 6-membered lactam ring. Deprotection of the amide group as described in scheme 1 yielded the desired analogues.

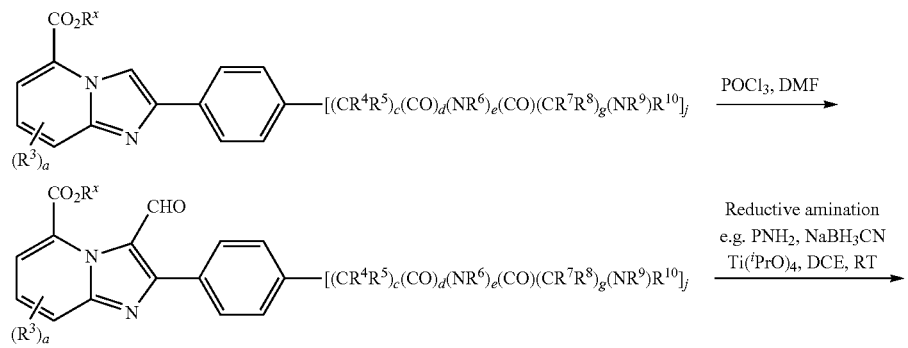

POCl₃, DMF

Reductive amination
e.g. PNH₂, NaBH₃CN
Ti($^i$PrO)₄, DCE, RT

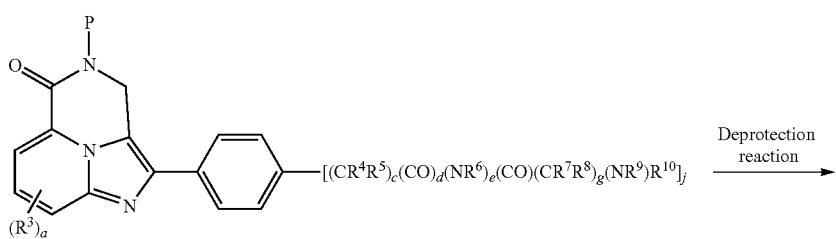

Deprotection reaction

P = Protecting group

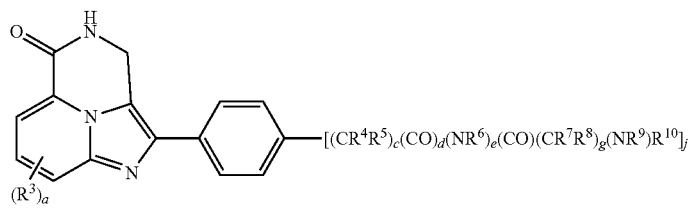

Scheme 3
A series of related analogues bearing a different heterocyclic system, the indazole, can be prepared from 3-bromo-2-bromomethyl benzoic ester by selective reduction of the carboxylic ester by treatment with DIBAL-H in toluene at 0° C. followed by protection of the resulting benzylic alcohol with a reagent such as TBDMSOTf, using 2,6-lutidine as a base. The indazole core was built following the procedure described in *Org. Lett.* 2000, 2 (4), 519, that is, reaction of the bromobenzyl intermediate with an aryl hydrazine in the presence of as base such as NaHMDS in THF followed by intramolecular cross-coupling reaction using Pd(OAc)$_2$/dppf as catalytic system. The protected hydroxyl group was converted to the carboxylic ester by deprotection reaction using TBAF followed by sequential oxidation to the carboxylic acid with MnO$_2$ and NaClO$_2$/NaH$_2$PO$_4$ and subsequent esterification using a reagent such as iodomethane in the presence of a base as Cs$_2$CO$_3$. Formation of the tricyclic core was performed following the same synthetic transformations described in scheme 1. Then, deprotection reaction of the amide group yielded the desired compound of formula wherein A and B are CH and D and E are N (scheme 3).

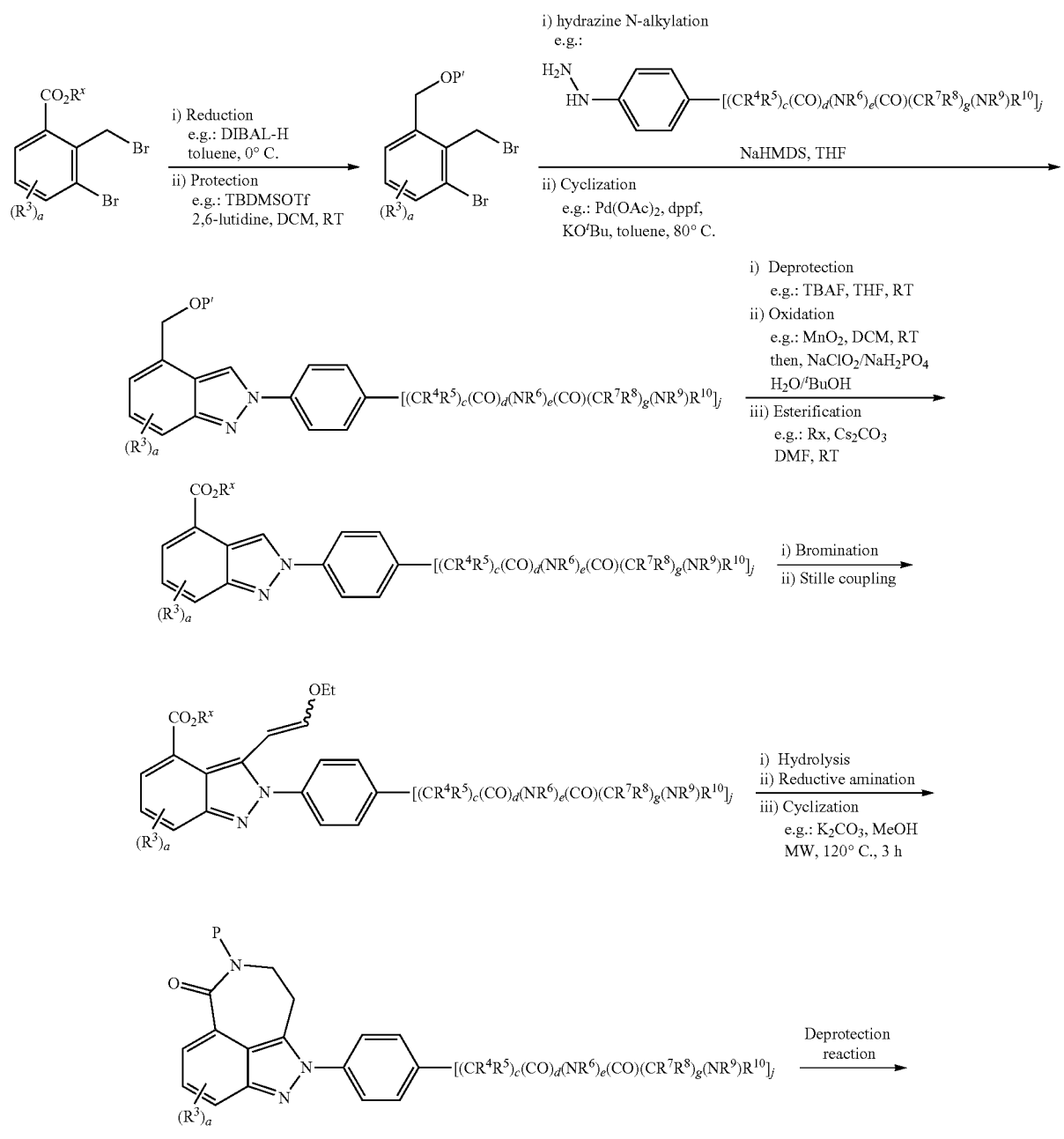

-continued

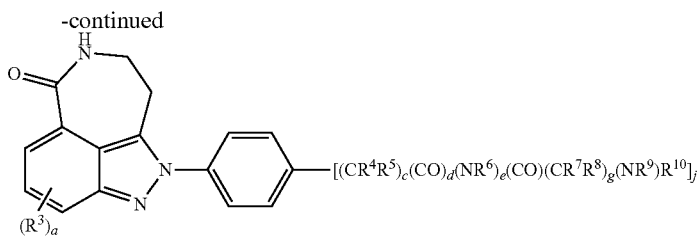

Scheme 4
A series of tricyclic inhibitors bearing an indolizine heterocyclic core, wherein A, D and E are CH and B is N can be prepared from 2-halonicotinic esters as shown in scheme 4. Sonogashira coupling with protected propargylamine followed by hydrogenation of the triple bond under $H_2$ atmosphere using Pd/C as catalyst and subsequent cyclization reaction led to the synthesis of a 6,7,8,9-tetrahydro-5H-pyrido[3,2-c]azepin-5-one. Treatment of this bicyclic intermediate with an α-bromoacetophenone in the presence of a base such as $CH_3ONa$ led to the formation of the desired compounds bearing the 3,4-dihydroazepino[3,4,5-hi]indolizin-1(2H)-one scaffold.

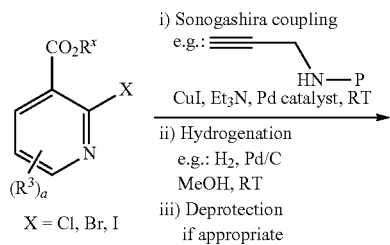

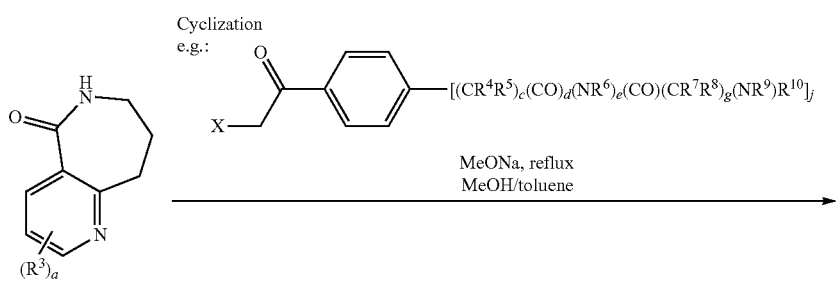

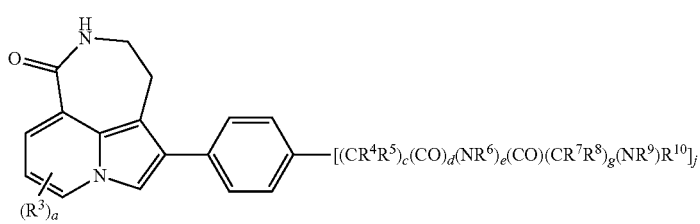

Scheme 5

Further manipulation of the aryl substituent allows the preparation of other derivatives as shown in scheme 5. For instance, when the aryl group has a nitrile substituent, this one can be reduced to the corresponding carbaldehyde by hydrogenolysis using HCO$_2$H and PtO$_2$ as catalyst. Later, reductive amination with the corresponding amine followed by deprotection of the amide group as described in scheme 1 afforded the desired benzylic amines.

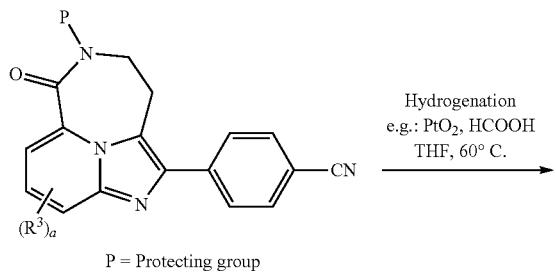

P = Protecting group

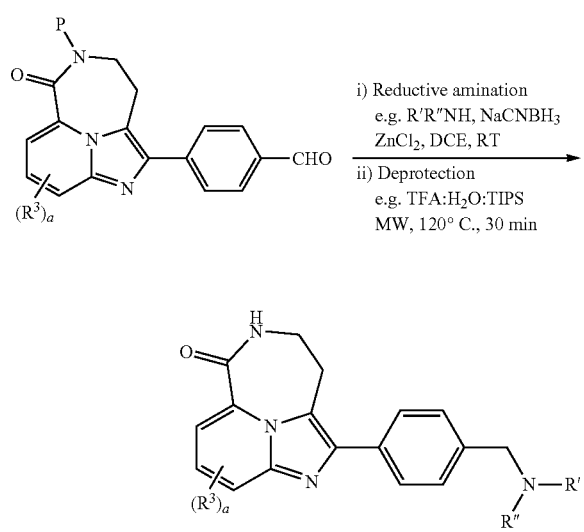

Scheme 6

Further derivatives can be prepared by late stage modification of these compounds, for instance, the nitrile group in the aryl ring can be reduced to a protected benzylic primary amine using reagents such as PtO$_2$ under H$_2$ atmosphere in the presence of (Boc)$_2$O. The resulting Boc-protected amine can be deprotected in acidic conditions. Conversion to the desired secondary or tertiary amine can be achieved by reductive amination with the appropriate aldehyde in the presence of NaBH$_3$CN.

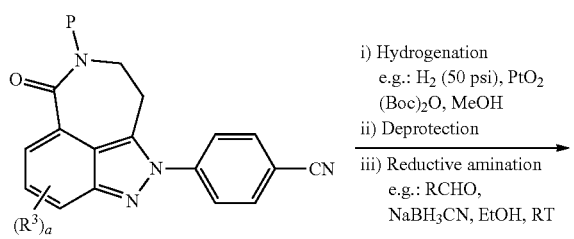

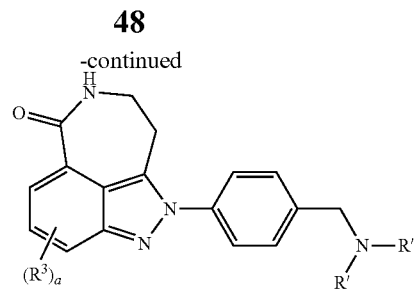

Scheme 7

If the aryl group has a carboxylic ester substituent, this one can be reduced to the corresponding benzylic alcohol by reaction with a hydride reagent such as DIBAL-H. Transformation of the hydroxyl group by preparation of a derivative such as mesylate, followed by treatment with the corresponding nucleophyle such as a primary or secondary amine afforded the desired compounds (Scheme 7).

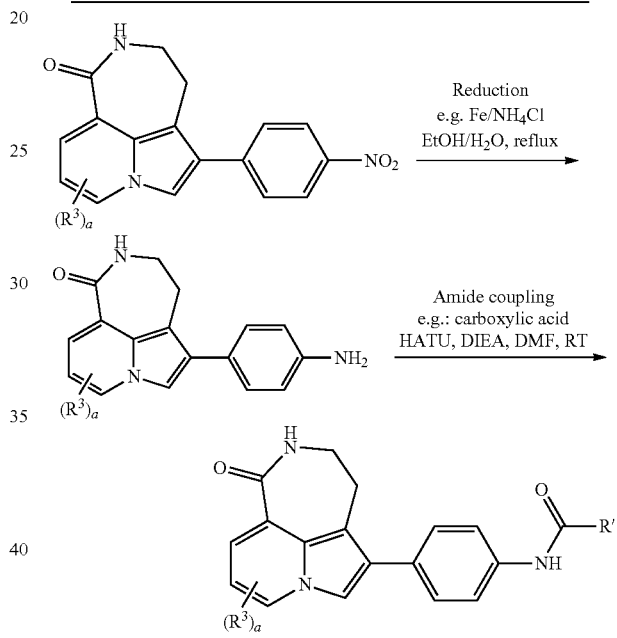

The exemplified compounds described herein were tested by the assays described below and were found to have an IC$_{50}$ value of less than 5 µM, particularly less than 200 nM.

PARP-1 Spa Assay

Working Reagents

Assay buffer: 100 mM Tris pH 8, 4 mM MgCl$_2$, 4 mM Spermine, 200 mM KCl, 0.04% Nonidet P-40.

Enzyme Mix: Assay buffer (12.5 ul), 100 mM DTT (0.5 ul), PARP-1 (5 nM, Trevigen 4668-500-01), H$_2$O (to 35 ul).

Nicotinamide-adenine dinucleotide (NAD)/DNA Mix: [$^3$H-NAD] (250 uCi/ml, 0.4 ul, Perkin-Elmer NET-443H), NAD (1.5 mM, 0.05 ul, SIGMA N-1511), Biotinylated-NAD (250 uM, 0.03 ul, Trevigen 4670-500-01), Activated calf thymus (1 mg/ml, 0.05 ul, Amersham Biosciences 27-4575), H$_2$O (to 10 ul).

Developing Mix: Streptavidin SPA beads (5 mg/ml, Amersham Biosciences RPNQ 0007) dissolved in 500 mM EDTA.

Experimental Design

The reaction is performed in 96-well microplate with a final volume of 50 uL/well. Add 5 ul 5% DMSO/compound solution, add enzyme mix (35 ul), start the reaction by adding NAD/DNA mix (10 uL) and incubate for 2 hrs at RT. Stop the reaction by adding developing mix (25 ul) and incubate 15 mM at RT. Measure using a Packard TOP COUNT instrument.

PARP-1 TCA Assay
Inhibitory Activity on Human PARP-1
Rationale

The study was designed to determine the potency of compounds for inhibiting poly(ADP-ribosylation) by hPARP1 upon presentation of a nicked DNA (i.e. Activated Calf Thymus). The $IC_{50}$ was determined in a TCA assay looking at the incorporation of [$^3$H]-NAD into the growing Poly-ADP-ribose (PAR) polymers and detection of the radioactivity incorporated in a polymer by scintillation counting.

Material and Methods

A 96 wells polypropylene microplate was prepared with serial dilutions of compounds (10 point over a 0.1 nM-50 nM concentration range 5% DMSO, 5 uL) or 5% DMSO. The enzymatic reaction was conducted in the presence of 25 mM Tris-HCl pH8.0, 1 mM $MgCl_2$, 50 mM KCl, 1 mM Spermine, 0.01% Nonidet P-40, 1 mM DTT, 1 ug/ml activated Calf Thymus DNA (Amersham Biosciences 27-4575) and 1 nM of human PARP-1 enzyme (Trevigen 4668-500-01). The reaction was initiated by adding 1 ug/ml Activated Calf Thymus DNA (Amersham Biosciences 27-4575), 0.4 ul ($2.2\times10^5$ DPM) of [$^3$H]-NAD (250 uCi/ml, Perkin Elmer NET-443H) and 1.5 uM NAD (Sigma #N-1511) in a total reaction volume of 50 ul. After 2 hours incubation at room temperature, the reaction was stopped by the addition of TCA (50 uL, 20%) and NaPPi (20 mM) and incubated for 10 min over ice. The resulting precipitate was filtered on Unifilter GF/B microplate (Perkin Elmer) and washed four times with 2.5% TCA using Harvester Filtermate 196 (Perkin Elmer). After addition of 50 ul of Microscint 20 (Perkin Elmer) the amount of radioactivity incorporated into the PARP polymers was read for each well on Perkin Elmer Top Count. $IC_{50}$ was calculated using 4P logistic fitting with ADA software based on the residual enzyme activity in the presence of increasing concentrations of compounds.

Proliferation Assay in BRCA-1 Silenced HeLa Cells

Abbreviations:
IMDM (Iscove's Modified Dulbecco's Media); RPMI (Roswell Park Memorial Institute Media); MOI (multiplicity of infection); GFP (green fluorescent protein); PBS (Phosphate Buffered Saline); FCS (fetal calf serum); and DMEM (Dulbecco's Modified Eagle's Medium).

Compounds of the present invention were also tested in an anti-proliferative assay in matched pair BRCA1wt and BRCA1-(shRNA) HeLa cells. The assay shows that PARP inhibitors are able to show selectivity with growth inhibition of the BRCA deficient cells. The majority of compounds showed $CC_{50}$'s less than 5 µM in BRCA1 deficient cells and a greater than 50 fold selectivity over the BRCA proficient cells. Some compounds showed $CC_{50}$ values in BRCA1 deficient cells of less than 1 µM.

The assay is based on the ability of living cells to convert a redox dye (resazurin) into a fluorescent end product (resofurin). The amount of resofurin produced is directly proportional to the cell number.

EXAMPLE 1

N-Methyl[4-(6-oxo-6,7,8,9-tetrahydro-2,7,9b-triazabenzo[cd]azulen-1-yl)phenyl]methanaminium trifluoroacetate (A7)

Step 1: Methy 6-aminopyridine-2-carboxylate (A1)

$H_2SO_4$ (3.0 eq.) was added to a suspension of 6-aminopyridine-2-carboxylic acid in MeOH (0.3 M). The reaction mixture was heated to reflux for 20 h. After cooling down, the solvent was reduced in vacuo and the residue was added to cooled sat. aq. $NaHCO_3$. The aqueous phase was extracted with DCM (2×) and the combined organic extracts were washed with brine and dried ($Na_2SO_4$). Evaporation of the solvent yielded the title compound as a white solid which was used in the next step without further purification. $^1$H NMR (400 MHz, DMSO-$d_6$, 300K) δ 7.50 (1H, t, J=7.8 Hz), 7.18 (1H, d, J=7.3 Hz), 6.65 (1H, d, J=8.3 Hz), 6.28 (2H, bs), 3.79 (3H, s). MS (ES$^+$) $C_7H_8N_2O_2$ requires: 152, found: 153 (M+H)$^+$.

Step 2: Methyl 2-(4-cyanophenyl)imidazo[1,2-a]pyridine-5-carboxylate (A2)

$NaHCO_3$ (1.0 eq.) was added to a solution of (A1) in i-PrOH (0.5 M), then 4-cyanophenacyl bromide (1.2 eq.) was added and the resulting reaction mixture was stirred at RT for 18 h, then heated to reflux for another 18 h. After cooling down, the solvent was reduced in vacuo and the residue partioned between sat. aq. $NaHCO_3$ and DCM. The aqueous phase was separated and extracted several times with DCM. The combined organic extracts were washed with brine and dried ($Na_2SO_4$). Evaporation of the solvent gave a residue which was triturated with hot EtOH and filtered to yield (31%) the title compound as a yellow solid. $^1$H NMR (400 MHz, DMSO-$d_6$, 300K) δ 9.31 (1H, s), 8.26 (2H, d, J=8.3 Hz), 8.00 (1H, d, J=9.0 Hz), 7.91 (2H, d, J=8.3 Hz), 7.85 (1H, d, J=7.0 Hz), 7.45 (1H, dd, J=9.0, 7.0 Hz), 4.00 (3H, s). MS (ES$^+$) $C_{16}H_{11}N_3O_2$ requires: 277, found: 278 (M+H)$^+$.

Step 3: Methyl 3-bromo-2-(4-cyanophenyl)imidazo[1,2-a]pyridine-5-carboxylate (A3)

$Br_2$ (1.0 eq.) was added, dropwise, to a solution of (A2) in DCM/AcOH=1:1 (0.05 M) at RT and the reaction mixture was stirred at RT for 2 h. The reaction mixture was quenched by the addition of sat. aq. $NaHCO_3$. The aqueous phase was separated and extracted several times with DCM. The combined organic extracts were washed with brine and dried ($Na_2SO_4$). Evaporation of the solvent gave a residue which was purified by flash column chromatography on silica using a gradient of EtOAc/Petroleum ether from 30:70 to 50:50 to yield (88%) the title compound as a white solid. $^1$H NMR (400 MHz, DMSO-$d_6$, 300K) δ 8.24 (2H, d, J=8.4 Hz), 8.00 (2H, d, J=8.6 Hz), 7.93 (1H, d, J=8.6 Hz), 7.55-7.45 (2H, m), 4.02 (3H, s). MS (ES$^+$) $C_{16}H_{10}BrN_3O_2$ requires: 355/357, found: 356/358 (M+H)$^+$.

Step 4: Methyl 2-(4-cyanophenyl)-3-[(E)-2-ethoxyvinyl]imidazo[1,2-a]pyridine-5-carboxylate (A4)

To a degassed solution of (A3) in DMF (0.1 M), $Cs_2CO_3$ (1.1 eq.), tris(dibenzenzylideneacetone)dipalladium(0) (0.05 eq.), tri-t-butylphosphonium tetrafluoroborate (0.15 eq.) and tributyl[(Z)-2-ethoxyvinyl]stannane (2.0 eq.) were added at RT and the reaction mixture was heated to 70° C. for 12 h. After cooling down, the solvent was reduced in vacuo and the residue partioned between sat. aq. $NaHCO_3$ and DCM. The aqueous phase was separated and extracted several times with DCM. The combined organic extracts were washed with brine and dried ($Na_2SO_4$). Evaporation of the solvent gave a residue which was purified by flash column on silica using a gradient of EtOAc/Petroleum ether from 30:70 to 50:50 to yield (74%) the title compound as a yellow oil, it is a mixture of regioisomers (cis/trans=4:1). $^1$H NMR (300 MHz, CDCl$_3$, 300K) δ 8.10 (2H, d, J=8.3 Hz), 7.90 (1H, d, J=8.7 Hz), 7.70

(2H, d, J=8.3 Hz), 7.40 (1H, d, J=6.4 Hz), 7.35-7.25 (1H, m), 6.32 (1H, d, J=6.7 Hz), 5.65 (1H, d, J=6.4 Hz), 3.97 (3H, s), 3.74 (2H, q, J=7.0 Hz), 1.03 (3H, t, J=7.0 Hz). MS (ES$^+$) $C_{20}H_{17}N_3O_3$ requires: 347, found: 348 (M+H)$^+$.

Step 5: 4-[7-(2,4-Dimethoxybenzyl)-6-oxo-6,7,8,9-tetrahydro-2,7,9b-triazabenzo[cd]azulen-1-yl]benzonitrile (A5)

A stirred solution of (A4) in a mixture of THF/H$_2$O 9:1 (0.2 M) was treated with Hg(OAc)$_2$ (1.5 eq.). After the reaction mixture was stirred at 50° C. for 3 h, freshly prepared sat. aq. KI was added and stirring was continued at RT for 10 min. Then, the reaction mixture was extracted with EtOAc, washed with sat. aq. Na$_2$S$_2$O$_4$ and dried (Na$_2$SO$_4$). Evaporation of the solvent gave methyl 2-(4-cyanophenyl)-3-(2-oxoethyl)imidazo[1,2-a]pyridine-5-carboxylate which was used in the next step without further purification. MS (ES$^+$) $C_{18}H_{13}N_3O_3$ requires: 319, found: 320 (M+H)$^+$.

To a solution of methyl 2-(4-cyanophenyl)-3-(2-oxoethyl)imidazo[1,2-a]pyridine-5-carboxylate in MeOH (0.2 M), 2,4-dimethoxybenzylamine (1.2 eq.) was added and the reaction mixture was stirred at RT for 2 h. Then, NaBH$_3$CN (1.5 eq.) was added and stirring was continued for 12 h. The solvent was reduced in vacuo and the residue partitioned between sat. aq. NaHCO$_3$ and DCM. The aqueous phase was separated and extracted several times with DCM. The combined organic extracts were washed with brine and dried (Na$_2$SO$_4$). Evaporation of the solvent gave a residue which was purified by flash column on silica using a gradient of EtOAc/Petroleum ether from 30:70 to 50:50 to yield (55% over two steps) the title compound. $^1$H NMR (600 MHz, DMSO-d$_6$, 330K) δ 7.96 (2H, d, J=8.4 Hz), 7.93 (2H, d, J=8.4 Hz), 7.85 (1H, d, J=8.8 Hz), 7.80 (1H, d, J=7.0 Hz), 7.45 (1H; dd, J=9.0, 7.0 Hz), 7.22 (1H, d, J=8.0 Hz), 6.62 (1H, d, J=2 Hz), 6.53 (1H; dd, J=8.4, 2.0 Hz), 4.73 (2H; s), 3.84 (3H, s), 3.77 (3H, s), 3.72-3.68 (2H, m), 3.46-3.42 (2H, m). MS (ES$^+$ $C_{26}H_{22}N_4O_3$ requires: 438, found: 439 (M+H)$^+$.

Step 6: 4-[7-(2,4-Dimethoxybenzyl)-6-oxo-6,7,8,9-tetrahydro-2,7,9b-triazabenzo[cd]azulen-1-yl]benzaldehyde (A6)

A suspension of (A5) and PtO$_2$ (0.1 eq.) in a solvent mixture of HCO$_2$H (80% sol. in water)/THF=2.5:1 (0.2 M) was heated to 60° C. for 4 h. After cooling, the catalyst was filtered through a pad of celite, then, the solvent was reduced in vacuo and the residue partioned between sat. aq. NaHCO$_3$ and DCM. The aqueous phase was separated and extracted several times with DCM. The combined organic extracts were washed with brine and dried (Na$_2$SO$_4$). Evaporation of the solvent gave the title compound which was used in the next step without further purification. $^1$H NMR (400 MHz, CDCl$_3$, 300K) δ 9.96 (1H, s), 7.78 (2H, d, J=7.8 Hz), 7.85-7.78 (3H, m), 7.72 (1H, d, J=8.6 Hz), 7.29 (1H, d, J=7.8 Hz), 7.27-7.18 (1H, m), 6.50-6.40 (2H, m), 4.78 (2H, s), 3.79 (3H, s), 3.75 (3H, s), 3.70-3.60 (2H, m), 3.30-3.20 (2H, m). MS (ES$^+$) $C_{26}H_{23}N_3O_4$ requires: 441, found: 442 (M+H)$^+$.

Step 7: N-Methyl[4-(6-oxo-6,7,8,9-tetrahydro-2,7,9b-triazabenzo[cd]azulen-1-yl)phenyl]methanaminium trifluoroacetate (A7)

To a solution of (A6) in DCE (0.1 M) was added Me$_2$NH.HCl (8 eq.) and ZnCl$_2$ (0.5 eq.) and the mixture was stirred for 12 h. To this solution NaBH$_3$CN (1.1 eq.) was added and stirring was continued for 12 h. The reaction mixture was quenched by the addition of sat. aq. NaHCO$_3$, then, the aqueous phase was separated and extracted several times with DCM. The combined organic extracts were washed with brine and dried (Na$_2$SO$_4$). Evaporation of the solvent gave a residue of 7-(2,4-dimethoxybenzyl)-1-{4-[(methylamino)methyl]phenyl}-8,9-dihydro-2,7,9b-tiazabenzo[cd]azulen-6(7H)-one which was used in the next step without further purification. MS (ES$^+$) $C_{27}H_{28}N_4O_3$ requires: 456, found: 457 (M+H)$^+$.

7-(2,4-dimethoxybenzyl)-1-{4-[(methylamino)methyl]phenyl}-8,9-dihydro-2,7,9b-triazabenzo[cd]azulen-6(7H)-one was dissolved in TFA/H$_2$O/TIPS=8.0:1.5:0.5 (0.1 M) and heated to 120° C. for 30 min at microwave apparatus. The solvent was reduced in vacuo and the residue was purified by preparative RP-HPLC (column: C18, using H$_2$O (+0.1% TFA) and MeCN (+0.1% TFA) as eluents, the desired fractions were lyophilized to afford (35% over two steps) the title compound. $^1$H NMR (300 MHz, CD$_3$CN, 300K) δ 9.00 (1H, bs), 8.18 (1H, d, J=8.4 Hz), 8.05 (1H, d, J=6.7 Hz), 7.80-7.70 (3H, m), 7.78-7.58 (3H, m), 4.22 (2H, s), 3.60-3.50 (2H, m), 3.45-3.35 (2H, m); 2.71 (3H, s). MS (ES$^+$) $C_{18}H_{18}N_4O$ requires: 306, found: 307 (M+H)$^+$.

EXAMPLE 2

N-Methyl[4-(5-oxo-4,5-dihydro-3H-1,4,8b-triazaacenaphthylen-2-yl)phenyl]methanaminium trifluoroacetate (B4)

Step 1: Methyl 2-(4-cyanophenyl)-3-formylimidazo[1,2-a]pyridine-5-carboxylate (B1)

POCl$_3$ (5.0 eq.) was added to a solution of Example 1, A2 in DMF (0.1 M) at RT. The reaction mixture was heated to reflux for 1 h. After cooling down, the reaction mixture was quenched by the addition of ice water, then, the aqueous phase was separated and extracted several times with DCM. The combined organic extracts were washed with brine and dried (Na$_2$SO$_4$). Evaporation of the solvent gave a residue which was purified by flash column on silica using a gradient of EtOAc/Petroleum ether from 40:60 to 70:30 to yield (58%) the title compound as a yellow powder. $^1$H NMR (400 MHz, DMSO-d$_6$, 300K) δ 9.80 (1H, s), 8.22-8.15 (3H, m), 8.04 (2H, d, J=8.4 Hz), 7.87 (1H, dd, J=8.8, 7.0 Hz), 7.70 (1H, d, J=7.0 Hz), 3.92 (3H, s). MS (ES$^+$) $C_{17}H_{11}N_3O_3$ requires: 305, found: 306 (M+H)$^+$.

Step 2: 4-[4-(2,4-Dimethoxybenzyl)-5-oxo-4,5-dihydro-3H-1,4,8b-triazaacenaphthylen-2-yl]benzonitrile (B2)

To a solution of (B1) in MeOH (0.2 M), 2,4-dimethoxybenzylamine (1.2 eq.) and Ti($^i$PrO)$_4$ (2.0 eq.) were added and the reaction mixture was stirred at RT for 2 h. Then, NaBH$_3$CN (1.5 eq.) was added and stirring was continued for 24 h. The solvent was reduced in vacuo and the residue pardoned between sat. aq. NaHCO$_3$ and DCM. The aqueous phase was separated and extracted several times with DCM. The combined organic extracts were washed with brine and dried (Na$_2$SO$_4$). Evaporation of the solvent gave a residue which was purified by flash column on silica using a gradient of EtOAc/Petroleum ether from 50:50 to 70:30 to yield (55%) the title compound as a yellow powder. $^1$H NMR (600 MHz, DMSO-d$_6$, 330K) δ 7.94 (2H, d, J=8.6 Hz), 7.90 (2H, d, J=8.6 Hz), 7.72 (1H, d, J=9.0 Hz), 7.47 (1H, d, J=7.0 Hz), 7.35 (1H, dd, J=8.4, 7.0 Hz), 7.23 (1H, d, J=8.3 Hz), 6.61 (1H, d, J=2.0

Hz), 6.48 (1H, dd, J=8.3, 2.0 Hz), 5.38 (2H, s), 4.72 (2H, s), 3.86 (3H, s), 3.74 (3H, s). MS (ES$^+$) $C_{25}H_{20}N_4O_3$ requires: 424, found: 425 (M+H)$^+$.

Step 3: 4-[4-(2,4-Dimethoxybenzyl)-5-oxo-4,5-dihydro-3H-1,4,8b-triazaacenaphthylen-2-yl]benzaldehyde (B3)

A suspension of (B2) and PtO$_2$ (0.1 eq.) in a solvent mixture of HCO$_2$H (80% sol. in water)/THF=2.5:1 (0.2 M) was heated to 60° C. for 4 h. After cooling, the catalyst was filtered through a pad of celite and the solvent was reduced in vacuo and the residue pardoned between sat. aq. NaHCO$_3$ and DCM. The aqueous phase was separated and extracted several times with DCM. The combined organic extracts were washed with brine and dried (Na$_2$SO$_4$). Evaporation of the solvent gave the title compound which was used in the next step without further purification. $^1$H NMR (400 MHz, DMSO-d$_6$, 300K) δ 10.0 (1H, s), 8.00 (4H, m), 7.75 (1H, d, J=9.0 Hz), 7.49 (1H, d, J=7.0 Hz), 7.38 (1H, dd, J=8.4, 7.0 Hz), 7.23 (1H, d, J=8.3 Hz), 6.61 (1H, d, J=2.0 Hz), 6.48 (1H, dd, J=8.3, 2.0 Hz), 5.40 (2H, s), 4.71 (2H, s), 3.86 (3H, s), 3.73 (3H, s). MS (ES$^+$) $C_{25}H_{21}N_3O_4$ requires: 427, found: 428 (M+H)$^+$.

Step 4: N-Methyl[4-(5-oxo-4,5-dihydro-3H-1,4,8b-triazaacenaphthylen-2-yl)phenyl]methanaminium trifluoroacetate (B4)

To a solution of (B3) in DCE (0.1 M) was added Me$_2$NH.HCl (8 eq.) and Ti($^i$PrO)$_4$ (2.0 eq.) and the mixture stirred at RT for 12 h. To this solution, NaBH$_3$CN (1.1 eq.) was added and stirring was continued for 12 h. The reaction mixture was quenched by the addition of sat. aq. NaHCO$_3$, then, the aqueous phase was separated and extracted several times with DCM. The combined organic extracts were washed with brine and dried (Na$_2$SO$_4$). Evaporation of the solvent gave a residue of 4-(2,4-dimethoxybenzyl)-2-{4-[(methylamino)methyl]phenyl}-3,4-dihydro-5H-1,4,8b-triazaacenaphthylen-5-one which was used in the next step without further purification. MS (ES$^+$) $C_{26}H_{26}N_4O_3$ requires: 442, found: 443 (M+H)$^+$.

4-(2,4-dimethoxybenzyl)-2-{4-[(methylamino)methyl]phenyl}-3,4-dihydro-5H-1,4,8b-triazaacenaphthylen-5-one was dissolved in TFA:H$_2$O:TIPS=8.0:1.5:0.5 (0.1 M) and heated to 120° C. for 30 min at microwave apparatus. The solvent was reduced in vacuo and the crude was purified by reverse phase HPLC (column: C18), using H$_2$O (+0.1% TFA) and MeCN (+0.1% TFA) as eluents, the desired fractions were lyophilized to yield (15% over two steps) the title compound. $^1$H NMR (400 MHz, DMSO-d$_6$, 300K) δ 8.76 (1H, bs), 8.68 (1H, s) 7.86 (2H, d, J=8.0 Hz), 7.68 (1H, d, J=9.0 Hz), 7.57 (2H, d, J=8.0 Hz), 7.37 (1H, d, J=7.0 Hz), 7.30 (1H, dd, J=9.0, 7.0 Hz), 5.28 (2H, s), 4.17 (2H, s), 2.60 (3H, s). MS (ES$^+$) $C_{17}H_{16}N_4O$ requires: 292, found: 293 (M+H)$^+$.

EXAMPLE 3

N-Methyl[4-(6-oxo-3,4,5,6-tetrahydro-2H-azepino[5,4,3-cd]indazol-2-yl)phenyl]methanaminium trifluoroacetate (C14)

Step [3-Bromo-2-(bromomethyl)phenyl]methanol (C1)

A solution of methyl 3-bromo-2-(bromomethyl)benzoate in dry toluene (0.45 M) was added dropwise to a solution of DIBAL-H (2 eq., 1 M in toluene) in dry toluene (0.9 M) at 0° C. The reaction mixture was stirred at 0° C. for 2 h. then, the reaction mixture was quenched with a solution of 1N HCl until pH 1 and the mixture was extracted with EtOAc. The combined organic extracts were washed with brine and dried (Na$_2$SO$_4$). Evaporation of the solvent yielded (96%) the title compound as a white powder, which was used in the next step without further purification. $^1$H NMR (300 MHz, DMSO-d$_6$, 300K) δ 7.66 (1H, d, J=8.0 Hz), 7.56 (1H, d, J=7.4 Hz), 7.32 (1H, t, J=7.6 Hz), 5.51 (1H, bt, J=5.4 Hz), 4.83 (2H, s), 4.70 (2H, bd, J=4.6 Hz).

Step 2: 5{[3-Bromo-2-(bromomethyl)benzyl]oxy}(tert-butyl)dimethylsilane (C2)

To a solution of (C1) in dry DCM (1 M) at 0° C., 2,6-lutidine (2 eq.) and TBDMSOTf (1.5 eq.) were added. The reaction mixture was stirred at RT for 45 min. Then, the resulting solution was partitioned between water and Et$_2$O and the organic phase was separated and dried (Na$_2$SO$_4$). Evaporation of the solvent gave a residue which was purified by flash column chromatography on silica, using hexane and Petroleum ether, to yield (93%) the title compound as colourless oil. $^1$H NMR (400 MHz, CDCl$_3$, 300K) δ 7.51 (1H, d, J=7.8 Hz), 7.41 (1H, d, J=7.6 Hz), 7.17 (1H, t, J=7.8 Hz), 4.86 (2H, s), 4.74 (2H, s), 0.95 (9H, s), 0.13 (6H, s).

Step 3: 4-{1-[2-Bromo-6-({[tert-butyl(dimethyl)silyl]oxy}methyl)benzyl]hydrazino}benzonitrile (C3)

(4-Cyanophenyl)hydrazine hydrochloride (1 eq.) was added to a solution of NaHMDS (2 eq., 1 M in THF) at 0° C. The reaction mixture was stirred at 0° C. for 15 min and then at RT for 1 h. Afterwards, the solution was cooled to 0° C. and a solution of (C2) in dry THF (1 M) was added. The ice-bath was removed and the reaction mixture was stirred at RT for 1 h. Then, the reaction mixture was diluted with DCM and washed with sat. aq. NaHCO$_3$, brine and dried (Na$_2$SO$_4$). Evaporation of the solvent gave a residue which was purified by purified by flash column chromatography on silica (EtOAc/Petroleum ether 1:24) to yield (77%) the title compound as yellow powder. $^1$H NMR (600 MHz, DMSO-d$_6$, 300K) δ 7.62-7.60 (3H, m), 7.53 (1H, d, J=7.7 Hz), 7.32 (1H, t, J=7.9 Hz), 7.22 (2H, d, J=9 Hz), 4.82 (2H, s), 4.77 (2H, s), 4.30 (2H, s), 0.90 (9H, s), 0.04 (6H, s). MS (ES$^+$) $C_{21}H_{28}BrN_3OSi$ required: 445/447, found: 446/448 (M+H)$^+$.

Step 4: 4-[4-({[tert-Butyl(dimethyl)silyl]oxy}methyl)-2H-indazol-2-yl]benzonitrile (C4)

To a solution of (C3) in dry toluene (0.28 M) was added sodium tert-butoxide (1.5 eq.), followed by dppf (0.075 eq.) and Pd(OAc)$_2$ (5% mol). The reaction mixture was heated to 80° C. for 35 min. After cooling down, the reaction mixture was directly loaded to a silica gel column and purified by flash column chromatography on silica (EtOAc/Petroleum ether 1:9) to yield (68%) the title compound as yellow powder. $^1$H NMR (300 MHz, CDCl$_3$, 300K) δ 8.59 (1H, s), 8.07 (2H, d, J=8.7 Hz), 7.83 (2H, d, J=8.5 Hz), 7.64 (1H, d, J=8.7 Hz), 7.32-7.28 (1H, m), 7.05-7.03 (1H, m), 4.99 (2H, s), 0.96 (9H, s), 0.13 (6H, s). MS (ES$^+$)$C_{21}H_{25}N_3OSi$ required: 363, found: 364 (M+H)$^+$.

Step 5: 4-[4-(Hydroxymethyl)-2H-indazol-2-yl]benzonitrile (C5)

TBAF (1.3 eq., 1M in THF) was added dropwise to a solution of (C4) in dry THF (0.1 M) and allowed to stir at RT for 1 h. The reaction mixture was diluted with EtOAc and washed with 1N HCl (2×), sat. aq. NaHCO$_3$, brine and dried (Na$_2$SO$_4$). Evaporation of the solvent yielded (100%) the title compound. $^1$H NMR (300 MHz, DMSO-d$_6$, 300K) δ 9.33 (1H, s), 8.36 (2H, d, 8.5 Hz), 8.11 (2H, d, J=8.2 Hz*–), 7.62 (1H, d, J=8.5 Hz), 7.36 (1H, t, J=7.3 Hz), 7.12 (1H, d, J=6.6 Hz), 5.36 (1H, bt, J=5.4 Hz), 4.84 (2H, d, J=5.2 Hz). MS (ES$^+$) C$_{15}$H$_{11}$N$_3$O required: 249, found: 250 (M+H)$^+$.

Step 6:
2-(4-Cyanophenyl)-2H-indazole-4-carboxylic acid (C6)

To a solution of (C5) in dry DCM (0.07 M) was added manganese (IV) oxide. The reaction mixture was stirred at RT for 2 h. Then, the suspension was filtered and the precipitated washed several times with DCM. The combined organic extracts were concentrated to dryness. The resulting crude was dissolved in a mixture of water/tert-butanol (1:1, 0.04 M). Afterwards, 2-methyl-2-butene (20 eq., 2 M in THF), NaH$_2$PO$_4$ (8 eq.) and NaClO$_2$ (8 eq.) were added. The reaction mixture was stirred at RT for 30 min. Then, the mixture was extracted with DCM (3×) and the organic extracts washed with brine (2×) and dried (Na$_2$SO$_4$). Evaporation of the solvent gave the title compound as a yellow powder that was used in the next step without further purification. $^1$H NMR (300 MHz, DMSO-d$_6$, 300K) δ 13.23 (1H, bs), 9.38 (1H, s), 8.45 (2H, d, J=7.3 Hz), 8.12-8.09 (3H, m), 7.91 (1H, d, J=6.8 Hz), 7.52 (1H, t, J=7.0 Hz). MS (ES$^+$) C$_{15}$H$_9$N$_3$O$_2$ required: 263, found: 264 (M+H)$^+$.

Step 7: Methyl 2-(4-cyanophenyl)-2H-indazole-4-carboxylate (C7)

Cs$_2$CO$_3$ (1.2 eq.) was added to a solution of (C6) in dry DMF (0.2 M). The resulting white suspension was stirred at RT for 30 min. After cooling down to 0° C., iodomethane (7 eq.) was added, then, the reaction mixture was stirred at RT for 90 min. The solution was diluted with EtOAc and washed with brine (2×) and dried (Na$_2$SO$_4$). Evaporation of the solvent afforded the title compound that was used in the next step without further purification. $^1$H NMR (300 MHz, CDCl$_3$, 300K) δ 9.02 (1H, s), 8.14 (2H, d, J=8.7 Hz), 8.01-7.95 (2H, m), 7.85 (2H, d, J=8.5 Hz), 7.42 (1H, t, J=7.4 Hz), 4.02 (3H, s). MS (ES$^+$) C$_{16}$H$_{11}$N$_3$O$_2$ required: 277, found: 278 (M+H)$^+$.

Step 8: Methyl 3-bromo-2-(4-cyanophenyl)-2H-indazole-4-carboxylate (C8)

(C8) was prepared following the general procedure reported in Example 1, step 3 and was used in the next step without further purification. $^1$H NMR (300 MHz, CDCl$_3$, 300K) δ 7.87-7.76 (6H, m), 7.43-7.38 (1H, m), 4.01 (3H, s). MS (ES$^+$) C$_{16}$H$_{10}$BrN$_3$O$_2$ requires: 355/357, found: 356/358 (M+H)$^+$.

Step 9: Methyl 2-(4-cyanophenyl)-3-[(2)-2-ethoxyvinyl]-2H-indazole-4-carboxylate (C9)

(C9) was prepared following the general procedure reported in Example 1, step 4 yielding (51% over four steps) the title compound as an yellow oil. It's a single regioisomer (Z). $^1$H NMR (400 MHz, CDCl$_3$, 300K) δ 7.79-7.74 (6H, m), 7.36-7.32 (1H, m), 6.14 (1H, d, J=7.1 Hz), 5.97 (1H, d, J=6.8 Hz), 3.93 (3H, s), 3.53 (2H, q, J=7.1 Hz), 0.90 (3H, t, J=7.0 Hz). MS (ES$^+$) C$_{20}$H$_{17}$N$_3$O$_3$ requires: 347, found: 348 (M+H)$^+$.

Step 10: Methyl 2-(4-cyanophenyl)-3-(2-oxoethyl)-2H-indazole-4-carboxylate (C10)

A stirred solution of (C9) in a mixture of THF/H$_2$O (9:1, 0.2 M) was treated with Hg(OAc)$_2$ (1.2 eq.). The reaction mixture was stirred at RT for 1 h. The reaction was quenched with freshly prepared sat aq. KI and the resulting solution was stirred at RT for 10 min. Then, the mixture was extracted with EtOAc and the organic phase was washed with brine and dried (Na$_2$SO$_4$). Evaporation of the solvent afforded the title compound, which was used in the next step without further purification. $^1$H NMR (400 MHz, DMSO-d$_6$, 300K) δ 9.74 (1H, s), 8.16 (2H, d, J=8.6 Hz), 8.05 (1H, d, J=8.1 Hz), 7.87 (1H, d, J=7.1 Hz), 7.82 (2H, d, J=8.6 Hz), 7.50 (1H, d, J=7.1 Hz), 4.46 (2H, s), 3.90 (3H, s). MS (ES$^+$) C$_{18}$H$_{13}$N$_3$O$_3$ requires: 319, found: 320 (M+H)$^+$.

Step 11: Methyl 2-(4-cyanophenyl)-3-{2-[(2,4-dimethoxybenzyl)amino]ethyl}-2H-indazole-4-carboxylate (C11)

To a solution of (C10) in dry EtOH (0.16 M), 2,4-dimethoxybenzylamine (1 eq.) was added and the reaction mixture was stirred at RT for 1 h. Then, NaBH$_3$CN (1 eq.) was added and stirring was continued for 12 h. The solvent was removed under reduced pressure and the residue dissolved in EtOAc washed with brine (2×) and dried (Na$_2$SO$_4$). Evaporation of the solvent afforded the title compound, which was used in the next step without further purification. MS (ES$^+$) C$_{27}$H$_{26}$N$_4$O$_4$ requires: 470, found: 471 (M+H)$^+$.

Step 12: 4-[5-(2,4-Dimethoxybenzyl)-6-oxo-3,4,5,6-tetrahydro-2H-azepino[5,4,3-cd]indazol-2-yl]benzonitrile (C12)

To a solution of (C11) in dry MeOH (0.2 M), K$_2$CO$_3$ (1.1 eq.) was added. The reaction mixture was heated under microwave conditions at 120° C. for 3 h. The solvent was removed under reduced pressure and the residue dissolved in EtOAc. The resulting organic solution was washed with brine (2×) and dried (Na$_2$SO$_4$). Evaporation of the solvent gave a residue which was purified by flash column chromatography on silica (EtOAc/Petroleum ether 2:3) to yield (30% over three steps) the title compound. $^1$H NMR (400 MHz, CDCl$_3$, 300K) δ 8.04 (1H, d, J=7.1 Hz), 7.89-7.77 (5H, m), 7.49 (1H, dd, J=8.6 and 7.1 Hz), 7.36 (1H, d, J=8.6 Hz), 6.51-6.49 (2H, m), 5.00-4.75 (2H, bs), 3.84-3.79 (8H, m), 3.30-3.00 (2H, bs). MS (ES$^+$) C$_{26}$H$_{22}$N$_4$O$_3$ requires: 438, found: 439 (M+H)$^+$.

Step 13: 4-[5-(2,4-Dimethoxybenzyl)-6-oxo-3,4,5,6-tetrahydro-2H-azepino[5,4,3-cd]indazol-2-yl]benzaldehyde (C13)

(C13) was prepared following the general procedure reported in Example 1 step 6, being used 0.2 eq. of PtO$_2$. The compound was used in the next step without further purification. $^1$H NMR (400 MHz, DMSO-d$_6$, 300K) δ 10.16 (1H, s), 8.18 (2H, d, J=8.6 Hz), 8.05 (2H, d, J=8.4 Hz), 7.94 (1H, d, J=8.6 Hz), 7.85 (1H, d, J=6.8 Hz), 7.54 (1H, dd, J=8.6 and 7.1 Hz), 7.20 (1H, d, J=8.3 Hz), 6.65 (1H, d, J=2.3 Hz), 6.55 (1H, dd, J=8.3 and 2.3 Hz), 4.74 (2H, bs), 3.87 (3H; s), 3.81 (3H; s), 3.78-3.75 (4H, m). MS (ES$^+$) C$_{26}$H$_{23}$N$_3$O$_4$ requires: 441, found: 442 (M+H)$^+$.

Step 14: N-Methyl[4-(6-oxo-3,4,5,6-tetrahydro-2H-azepino[5,4,3-cd]indazol-2-yl)phenyl]methanaminium trifluoroacetate (C14)

(C14) was prepared following the general procedure reported in Example 1 step 7 yielding (3% over three steps)

the title compound as a pale yellow powder. $^1$H NMR (600 MHz, DMSO-$d_6$, 300K) S 8.89 (2H, bs), 8.31 (1H, t, J=5.6 Hz), 7.92-7.90 (3H, m), 7.78 (1H, d, J=7.0 Hz), 7.74 (2H, d, J=8.4 Hz), 7.50 (1H, dd, J=8.5 and 7.0 Hz), 4.32-4.28 (2H, m), 3.53 (2H, q, J=5.3 Hz), 3.32-3.27 (2H, m); 2.69-2.65 (3H, m). MS (ES$^+$) $C_{18}H_{18}N_4O$ requires: 306, found: 307 (M+H)$^+$.

EXAMPLE 4

N,N-Dimethyl[4-(6-oxo-3,4,5,6-tetrahydro-2H-azepino[5,4,3-cd]indazol-2-yl)phenyl]methanaminium trifluoroacetate (D1)

PtO$_2$ (0.5 eq.) was added to a solution of Example 3, (C12) and (Boc)$_2$O (1.5 eq.) in MeOH and the reaction mixture was attached to a Parr apparatus at a pressure of 50 psi for 12 h. Then, the reaction mixture was filtered and solvent was evaporated under reduced pressure giving a crude that was dissolved in EtOAc, washed with brine and dried (Na$_2$SO$_4$). Evaporation of the solvent afforded a residue of tert-butyl {4-[5-(2,4-dimethoxybenzyl)-6-oxo-3,4,5,6-tetrahydro-2H-azepino[5,4,3-cd]indazol-2-yl]benzyl}carbamate, which was used without further purification. MS (ES) $C_{31}H_{34}N_4O_5$ requires: 542, found: 543 (M+H)$^+$.

tert-butyl {-4-[5-(2,4-dimethoxybenzyl)-6-oxo-3,4,5,6-tetrahydro-2H-azepino[5,4,3-cd]indazol-2-yl] benzyl}carbamate was dissolved in a mixture of TFA:TIPS:H$_2$O (4:0.3:2.4, 0.2 M) and was stirred at 100° C. for 15 min at a microwave apparatus. The solution was loaded into a SCX cartridge and the washed off with a methanolic solution of ammonia. Evaporation of the solvent gave a residue of 2-[4-(aminomethyl)phenyl]-2,3,4,5-tetrahydro-6H-azepino [5,4,3-cd]indazol-6-one, which was used without further purification. MS (ES$^+$) $C_{17}H_{16}N_4O$ requires: 292, found: 293 (M+H)$^+$.

To a solution of 2-[4-(aminomethyl)phenyl]-2,3,4,5-tetrahydro-6H-azepino[5,4,3-cd]indazol-6-one in EtOH (0.03 M), formaldehyde (2 eq., 37% in water) and NaBH$_3$CN (1.5 eq.) were added. The reaction mixture was stirred at RT for 1 h. Then, solvent was removed in vacuum and the crude was purified by preparative RP-HPLC, using H$_2$O (+0.1% TFA) and MeCN (+0.1% TFA) as eluents (column: Water X-Terra C18). The pooled product fractions were lyophilized to yielding (2%) the title compound. $^1$H NMR (400 MHz, CD$_3$CN, 300K) δ 12.10 (1H, bs), 7.78 (1H, d, J=8.6 Hz), 7.75 (1H, d, J=7.0 Hz), 7.69-7.63 (4H, m), 7.40-7.36 (1H, m), 6.75 (1H, bs), 4.22 (2H, m), 3.54-3.48 (2H, m), 3.31-3.17 (2H, m), 2.70 (6H, s). MS (ES$^+$) $C_{19}H_{20}N_4O$ requires: 320, found: 321 (M+H)$^+$.

EXAMPLE 5

[4-(8-Fluoro-6-oxo-3,4,5,6-tetrahydro-2H-azepino[5,4,3-cd]indazol-2-yl)phenyl]-N,N-dimethylmethanaminium trifluoroacetate (E18)

Step 1: 5-Fluoro-2-methyl-3-nitrobenzoic acid (E1)

A solution of 5-fluoro-2-methylbenzoic acid (from Matrix Scientific) in H$_2$SO$_4$ conc. (0.83 M) was cooled down to −10° C. Then, a mixture of fuming HNO$_3$ conc. (2 eq.) and H$_2$SO$_4$ conc. (4 eq.) was added dropwise. After complete addition, the mixture was stirred at 0° C. for 1 h. The reaction mixture was poured onto ice/water and stirred for 10 min and then extracted with EtOAc. The combined organic layers were washed with brine, dried (Na$_2$SO$_4$) and solvent was removed in vacuo yielding the title compound as a yellow solid that was used without further purification in the next step. $^1$H NMR (300 MHz, DMSO-$d_6$, 300 K) δ 13.86 (1H, bs), 8.09 (1H, dd, J=8.0 and 2.6 Hz), 7.90 (1H, dd, J=8.7 and 2.4 Hz), 2.50 (3H, s).

Step 2: 3-Amino-5-fluoro-2-methylbenzoic acid (E2)

To a solution of (E1) in MeOH (0.5 M), Pd on carbon (10 wt %, 0.2 eq.) was added. The reaction mixture was equipped with H$_2$ atmosphere and the resulting suspension was stirred at RT for 24 h. The precipitated was filtered off and the filtrate was evaporated to dryness to yield the title compound as a brown powder that was used without further purification in the next step. $^1$H NMR (400 MHz, DMSO-$d_6$, 300 K) δ 8.39 (1H, bs), 7.98 (1H, dd, J=11.1 and 2.8 Hz), 6.85 (1H, dd, J=9.1 and 2.8 Hz), 3.21 (2H, s), 2.19 (3H, s).

Step 3: 3-Bromo-5-fluoro-2-methylbenzoic acid (E3)

tert-Butyl nitrite (1.5 eq.) was added to a slurry of anhydrous CuBr$_2$ (1.1 eq.) in dry acetonitrile (0.2 M) cooled to 0° C. Then, (E2) was added to the resulting dark green mixture. After stirring at 0° C. for 2 h, the reaction mixture was warmed to RT and stirred at this temperature overnight. Then, the reaction mixture was concentrated under vacuum and the resulting residue dissolved in EtOAc. The organic phase was washed with sat. aq. NH$_4$Cl, brine and dried (Na$_2$SO$_4$). Evaporation of the solvent under reduced pressure yielded the title compound that was used without further purification in the next step. MS (ES$^-$) $C_8H_6BrFO_2$ required: 232/234, found: 231/233 (M−H)$^-$.

Step 4: Methyl 3-bromo-5-fluoro-2-methylbenzoate (E4)

K$_2$CO$_3$ (1.2 eq.) was added to a solution of (E3) in DMF (0.26 M) and the resulting suspension was stirred at RT for 30 min. Then, iodomethane (1.2 eq.) was added and the reaction mixture was stirred at RT overnight. The solution was diluted in EtOAc and the organic phase was washed with brine and dried (Na$_2$SO$_4$). Solvent was removed in vacuo giving a residue that was purified by flash chromatography column on silica (EtOAc/Petroleum ether 1:49) yielding (31% over 4 steps) the title compound as a yellow oil. $^1$H NMR (400 MHz, CDCl$_3$, 300 K) δ 7.74 (1H, dd, J=8.4 and 2.8 Hz), 7.60 (1H, dd, J=7.3 and 2.5 Hz), 3.95 (3H, s), 2.59 (3H, s).

Step 5: Methyl 3-bromo-2-(bromomethyl)-5-fluorobenzoate (E5)

A suspension of (E4), NBS (1.2 eq.) and benzoyl peroxide (0.1 eq.) in CCl$_4$ (0.28 M) was heated to reflux for 4.5 h. Afterwards, the reaction mixture was cooled down to 0° C. and the solid filtered off. The solid was washed with Et$_2$O and the filtrate was washed sequentially with 1 M Na$_2$S$_2$O$_3$, brine and dried (Na$_2$SO$_4$). Evaporation of the solvent under reduced pressure afforded the title compound that was used without further purification in the next step. $^1$H NMR (400 MHz, CDCl$_3$, 300 K) δ 7.63 (1H, dd, J=8.6 and 2.8 Hz), 7.52 (1H, dd, J=7.4 and 2.8 Hz), 5.10 (2H, s), 3.97 (3H, s).

Step 6: {[3-Bromo-2-(bromomethyl)-5-fluorobenzyl] oxy}(tert-butyl)dimethylsilane (E6)

A solution of DIBAL-H (2 eq., 1M in toluene) in dry toluene (0.72 M) was cooled to 0° C. Then, a solution of (E5) in dry toluene (0.45 M) was added dropwise, and the resulting solution was stirred at 0° C. for 2 h. The reaction solution was quenched with a solution of 1 N HCl and the crude was extracted with EtOAc. The organic phase was washed with brine and dried ($Na_2SO_4$). The solvent was evaporated to dryness to afford [3-bromo-2-(bromomethyl)-5-fluorophenyl]methanol as a white powder, which was dissolved in DCM (1 M) at 0° C. The resulting solution was treated with 2,6-lutidine (2 eq.) and TBDMSTf (1.5 eq.). The reaction mixture was stirred at RT for 45 min. Then, the resulting solution was partitioned between water and $Et_2O$ and the organic phase was separated and dried ($Na_2SO_4$). Evaporation of the solvent gave a residue which was purified by flash column chromatography on silica, using hexane and Petroleum ether, to yield (83%) the title compound as colourless oil. $^1$H NMR (400 MHz, $CDCl_3$, 300K) δ 7.15-7.12 (2H, m), 4.74 (2H, s), 4.53 (2H, s), 0.86 (9H, s), 0.04 (6H, s).

Step 7: 4-{1-[2-Bromo-6-({[tert-butyl(dimethyl)silyl]oxy}methyl)-4-fluorobenzyl]hydrazino}benzonitrile (E7)

(E7) was prepared following the general procedure reported in Example 3 step 3 yielding the title compound as a yellow powder. $^1$H NMR (400 MHz, DMSO-$d_6$, 300K) δ 7.56 (2H, d, J=8.8 Hz), 7.50 (1H, dd, J=8.2 and 2.6 Hz), 7.28 (1H, dd, J=10.0 and 2.8 Hz), 7.18 (2H, d, J=9.1 Hz), 4.77 (2H, s), 4.66 (2H, s), 4.27 (2H, s), 0.87 (9H, s), 0.03 (6H, s). MS ($ES^+$) $C_{21}H_{27}BrFN_3OSi$ required: 463/465, found: 464/466 $(M+H)^+$.

Step 8: 4-[4-({[tert-Butyl(dimethyl)silyl]oxy}methyl)-6-fluoro-2H-indazol-2-yl]benzonitrile (E8)

(E8) was prepared following the general procedure reported in Example 3 step 4 yielding (42% over two steps) the title compound as a yellow powder. $^1$H NMR (300 MHz, $CDCl_3$, 300K) δ 8.55 (1H, s), 8.03 (2H, d, J=7.6 Hz), 7.82 (2H, d, J=8.1 Hz), 7.21 (1H, bd, J=9.7 Hz), 6.91 (1H, bd, J=9.5 Hz), 4.97 (2H, s), 0.97 (9H, s), 0.14 (6H, s). MS ($ES^+$) $C_{21}H_{24}FN_3OSi$ required: 381, found: 382 $(M+H)^+$.

Step 9: 4-[6-Fluoro-4-(hydroxymethyl)-2H-indazol-2-yl]benzonitrile (E9)

(E9) was prepared following the general procedure reported in Example 3 step 5 yielding (100%) the title compound. $^1$H NMR (300 MHz, DMSO-$d_6$, 300K) δ 9.40 (1H, s), 8.34 (2H, d, J=8.5 Hz), 8.12 (2H, d, J=7.6 Hz), 7.36 (1H, d, J=9.9 Hz), 7.03 (1H, d, J=10.3 Hz), 5.56-5.53 (1H, m), 4.87 (2H, d, J=5.0 Hz). MS ($ES^+$) $C_{15}H_{10}FN_3O$ required: 267, found: 268 $(M+H)^+$.

Step 10: 2-(4-Cyanophenyl)-6-fluoro-2H-indazole-4-carboxylic acid (E10)

(E10) was prepared following the general procedure reported in Example 3 step 6 and was used in the next step without further purification. $^1$H NMR (300 MHz, DMSO-$d_6$, 300K) δ 13.62 (1H, bs), 9.44 (1H, s), 8.44 (2H, d, J=8.7 Hz), 8.11 (2H, d, J=8.5 Hz), 7.88 (1H, d, J=9.5 Hz), 7.71 (1H, d, J=9.7 Hz). MS ($ES^+$) $C_{16}H_8FN_3O_2$ required: 261, found: 262 $(M+H)^+$.

Step 11: Methyl 2-(4-cyanophenyl)-6-fluoro-2H-indazole-4-carboxylate (E11)

(E11) was prepared following the general procedure reported in Example 3 step 7 and was used in the next step without further purification. $^1$H NMR (300 MHz, $CDCl_3$, 300K) δ 8.95 (1H, s), 8.05 (2H, d, J=8.5 Hz), 7.78 (2H, d, J=8.5 Hz), 7.68-7.66 (1H, m), 7.53-7.50 (1H, m), 3.96 (3H, s). MS ($ES^+$) $C_{16}H_{10}FN_3O_2$ required: 295, found: 296 $(M+H)^+$.

Step 12: Methyl 3-bromo-2-(4-cyanophenyl)-6-fluoro-2H-indazole-4-carboxylate (E12)

(E12) was prepared following the general procedure reported in Example 3 step 8 and was used in the next step without further purification. $^1$H NMR (300 MHz, $CDCl_3$, 300K) δ 7.89-7.76 (4H, m), 7.62-7.49 (2H, m), 4.02 (3H, s).

Step 13: Methyl 2-(4-cyanophenyl)-3-[(2)-2-ethoxyvinyl]-6-fluoro-2H-indazole-4-carboxylate (E13)

(E13) was prepared following the general procedure reported in Example 3 step 9 yielding (6% over four steps) the title compound as a yellow powder. NMR (300 MHz, $CDCl_3$, 300K) δ 7.88-7.72 (4H, m), 7.55-7.45 (2H, m), 6.15 (1H, d, J=6.8 Hz), 5.92 (1H, d, J=6.8 Hz), 3.94 (3H, s), 3.55 (2H, q, J=7.2 Hz), 0.91 (3H, t, J=7.0 Hz). MS ($ES^+$) $C_{20}H_{16}FN_3O_3$ requires: 365, found: 366 $(M+H)^+$.

Step 14: Methyl 2-(4-cyanophenyl)-6-fluoro-3-(2-oxoethyl)-2H-indazole-4-carboxylate (E14)

(E14) was prepared following the general procedure reported in Example 3 step 10 and was used in the next step without further purification. $^1$H NMR (300 MHz, DMSO-$d_6$, 300K) δ 9.72 (1H, s), 8.16 (2H, d, J=8.3 Hz), 7.88-7.80 (3H, m), 7.69 (1H, d, J=10.3 Hz), 4.45 (2H, s), 3.92 (3H, s). MS ($ES^+$) $C_{18}H_{12}FN_3O_3$ requires: 337, found: 338 $(M+H)^+$.

Step 15: Methyl 2-(4-cyanophenyl)-3-{2-[(2,4-dimethoxybenzyl)amino]ethyl}-6-fluoro-2H-(E15)

(E15) was prepared following the general procedure reported in Example 3 step 11 and was used in the next step without further purification. MS ($ES^+$) $C_{27}H_{25}FN_4O_4$ requires: 488, found: 489 $(M+H)^+$.

Step 16: 4-[5-(2,4-Dimethoxybenzyl)-8-fluoro-6-oxo-3,4,5,6-tetrahydro-2H-azepino[5,4,3-cd]indazol-2-yl]benzonitrile (E16)

(E16) was prepared following the general procedure reported in Example 3 step 12 yielding (25% over three steps) the title compound. NMR (400 MHz, $CDCl_3$, 300K) δ 7.84 (3H, m), 7.74 (2H, d, J=8.8 Hz), 7.43 (1H, dd, J=8.8 and 2.0 Hz), 7.35 (1H, d, J=9.1 Hz), 6.51-6.49 (2H, m), 5.00-4.75 (2H, bs), 3.87-3.80 (8H, m), 3.20-2.95 (2H, bs). MS ($ES^+$) $C_{26}H_{21}FN_4O_3$ requires: 456, found: 457 $(M+H)^+$.

Step 17: 4-[5-(2,4-Dimethoxybenzyl)-8-fluoro-6-oxo-3,4,5,6-tetrahydro-2H-azepino[5,4,3-cd]indazol-2-yl]benzaldehyde (E17)

(E17) was prepared following the general procedure reported in Example 3 step 13 and was used in the next step without further purification. MS ($ES^+$) $C_{26}H_{22}FN_3O_4$ requires: 459, found: 460 $(M+H)^+$.

Step 18: [4-(8-Fluoro-6-oxo-3,4,5,6-tetrahydro-2H-azepino[5,4,3-cd]indazol-2-yl)phenyl]-N,N-dimethylmethanaminium trifluoroacetate (E18)

(E18) was prepared following the general procedure reported in Example 3 step 14 yielding (2.5% over two steps)

the title compound as a white powder. $^1$H NMR (400 MHz, DMSO-d$_6$, 300K) δ 10.29 (1H, bs), 8.44 (1H, bs), 7.85 (2H, d, J=7.6 Hz), 7.73 (2H, d, J=7.8 Hz), 7.64 (1H, d, J=9.4 Hz), 7.51 (1H, d, J=9.8 Hz), 4.41 (2H, s), 3.49 (2H, bs), 3.27 (2H, bs); 2.78 (6H, s). MS (ES$^+$) C$_{19}$H$_{19}$FN$_4$O requires: 338, found: 339 (M+H)$^+$.

EXAMPLE 6

3-[4-8-Fluoro-6-oxo-3,4,5,6-tetrahydro-2H-azepino [5,4,3-cd]indazol-2-yl)phenyl]piperidinium trifluoroacetate (F14); 8-fluoro-2-{4-[3R)-piperidin-3-yl] phenyl}-2,3,4,5-tetrahydro-6H-azepino[5,4,3-cd] indazol-6-one (F15); and 8-fluoro-2-{4-[(3S)-piperidin-3-yl]phenyl}-2,3,4,5-tetrahydro-6H-azepino[5,4,3-cd]indazol-6-one (F16)

Step 1: 1-Benzyl-3-(4-chlorophenyl)piperidine (F1)

To a solution of 3-(4-chlorophenyl)piperidine in MeOH (0.2 M), benzaldehyde (2.1 eq.) was added and the reaction mixture was stirred at RT for 1 h. Then, it was cooled to 0° C. and NaBH$_3$CN (3 eq.) was added. The mixture was allowed to warm to RT and stirred for 1 h. Evaporation of the solvent gave a residue that was partitioned between sat. aq. NaHCO$_3$ and EtOAc and the organic phase was separated and dried (Na$_2$SO$_4$). Evaporation of the solvent gave a crude that was purified by flash chromatography column on silica (Petroleum ether to EtOAc/Petroleum ether 1:19) yielding (62%) the title compound as a yellow powder. $^1$H NMR (300 MHz, DMSO-d$_6$, 300K) δ 7.36-7.17 (9H, m), 3.48 (2H, s), 2.87-2.68 (3H, m), 2.05-1.91 (2H, m), 1.86-1.75 (1H, m), 1.74-1.50 (2H, m), 1.48-1.3 (1H, m). MS (ES$^+$) C$_{18}$H$_{20}$ClN required: 285, found: 286 (M+H)$^+$.

Step 2: Diphenylmethanone [4-(1-benzylpiperidin-3-yl)phenyl]hydrazone (F2)

A mixture of (F1), benzophenone hydrazone (1.8 eq.), ground NaOH (1.4 eq.), Pd(AcO)$_2$ (0.05 eq.) and XPhos (0.1 eq.) in degassed $^t$BuOH (0.18 M) was stirred under argon at RT for 20 min and then was heated at 80° C. for 3 h. After cooling down, evaporation of the solvent gave a residue that was dissolved in DCM and washed with sat. aq. NH$_4$Cl (2×) and sat. aq. NaHCO$_3$ (2×) and dried (Na$_2$SO$_4$). Evaporation of the solvent gave a crude that was purified by flash chromatography column on silica (EtOAc/Petroleum ether 2:98 to 1:4) yielding (90%) the title compound as a yellow foam. $^1$H NMR (300 MHz, DMSO-d$_6$, 300K) δ 8.68 (1H, s), 7.67-7.49 (3H, m), 7.46-7.39 (2H, m), 7.37-7.25 (10H, m), 7.13 (2H, d, J=8.3 Hz), 7.04 (2H, d, J=8.3 Hz), 3.47 (2H, s), 2.92-2.75 (2H, m), 2.70-2.56 (1H, m), 2.06-1.86 (2H, m), 1.83-1.50 (3H, m), 1.48-1.32 (1H, m). MS (ES$^+$) C$_{31}$H$_{31}$N$_3$ required: 445, found: 446 (M+H)$^+$.

Step 3: 1-Benzyl-3-(4-diazan-2-iumylphenyl)piperidinium dichloride (F3)

A suspension of (F2) in EtOH/conc. HCl (1:10, 0.8 M solution) was stirred overnight at RT. Then, the reaction mixture was extracted with Et$_2$O (3×) and the aqueous phase was concentrated under reduced pressure and dried under high vacuum pump to afford (80%) the title compound as a beige solid. $^1$H NMR (300 MHz, DMSO-d$_6$, 300K) δ 10.84 (1H, s), 10.16 (3H, s), 8.22 (1H, s), 7.66-7.55 (2H, m), 7.48-7.39 (3H, m), 7.15 (2H, d, J=8.1 Hz), 6.95 (2H, d, J=8.1 Hz), 4.28 (2H, s), 3.38-3.22 (2H, m), 3.20-3.06 (1H, m), 3.05-2.80 (2H, m), 2.04-1.76 (3H, m), 1.69-1.52 (1H, m). MS (ES$^+$) C$_{18}$H$_{25}$Cl$_2$N$_3$ required: 281, found: 282 (M+H)$^+$.

Step 4: 1-Benzyl-3-(4-{1-[2-bromo-6-({[tert-butyl (dimethyl)silyl]oxy}methyl)-4-fluorobenzyl] hydrazino}phenyl)piperidine (F4)

(F4) was prepared by reaction of (E6) with (F3) following the general procedure reported in Example 3 step 3 yielding (73%) the title compound as a yellow oil. $^1$H NMR (300 MHz, CDCl$_3$, 300K) δ 7.32-7.23 (7H, m), 7.17-7.09 (4H, m), 4.83 (2H, s), 4.52 (2H, s), 3.54 (2H, s), 3.32 (2H, bs), 3.00-2.90 (2H, m), 2.84-2.74 (1H, m), 2.05-1.89 (3H, m), 1.76-1.78 (2H, m), 1.47-1.38 (1H, m), 0.90 (9H, s), 0.04 (6H, s). MS (ES$^+$) C$_{32}$H$_{43}$BrFN$_3$OSi required: 611/613, found: 612/614 (M+H)$^+$.

Step 5: 2-[4-(1-Benzylpiperidin-3-yl)phenyl]-4-({ [tert-butyl(dimethyl)silyl]oxy}methyl)-6-fluoro-2H-indazole (F5)

(F5) was prepared following the general procedure reported in Example 3 step 4 yielding (60%) the title compound as a yellow oil. $^1$H NMR (300 MHz, CDCl$_3$, 300K) δ 8.43 (1H, s), 7.76 (2H, d, J=8.5 Hz), 7.38-7.32 (6H, m), 7.29-7.22 (2H, m), 6.88 (1H, bd, J=9.8 Hz), 4.98 (2H, s), 3.56 (2H, s), 3.03-2.92 (3H, m), 2.13-1.94 (3H, m), 1.77-1-73 (3H, m), 0.97 (9H, s), 0.14 (6H, s). MS (ES$^+$) C$_{32}$H$_{40}$FN$_3$OSi required: 529, found: 530 (M+H)$^+$.

Step 6: tert-Butyl 3-{4-[4-({[tert-butyl(dimethyl) silyl]oxy}methyl)-6-fluoro-2H-indazol-2-yl] phenyl}piperidine-1-carboxylate (F6)

Pd(OH)/C (10 wt %, 0.1 eq.) was added to a solution of (F5) and (Boc)$_2$O (1.1 eq.) in EtOH (0.1 M), the reaction mixture was stirred under a H$_2$ atmosphere at RT for 10 hr. Then, it was filtered and solvent removed under reduced pressure giving a residue that was purified by flash chromatography column on silica (EtOAc/Petroleum ether 1:19) yielding (67%) the title compound as a white foam. $^1$H NMR (300 MHz, CDCl$_3$, 300K) δ 8.45 (1H, s), 7.76 (21-1, d, J=8.3 Hz), 7.38 (2H, d, J=8.5 Hz), 7.24-7.22 (1H, m), 6.89 (1H, dd, J=9.9 and 1.0 Hz), 4.98 (2H, s), 4.30-4.10 (2H, m), 2.90-2.70 (3H, m), 2.09-2.05 (1H, m), 1.81-1.62 (3H, m), 1.48 (9H, s), 0.97 (9H, s), 0.14 (6H, s). MS (ES$^+$) C$_{30}$H$_{42}$FN$_3$O$_3$Si required: 539, found: 540 (M+H)$^+$.

Step 7: tert-Butyl 3-{4-[6-fluoro-4-(hydroxymethyl)-2H-indazol-2-yl]phenyl}piperidine-1-carboxylate (F7)

(F7) was prepared following the general procedure reported in Example 3 step 5 yielding (100%) the title compound. $^1$H NMR (400 MHz, CDCl$_3$, 300K) δ 8.50 (1H, s), 7.78 (2H, d, J=7.9 Hz), 7.35 (2H, d, J=8.1 Hz), 7.26-7.24 (1H, m, overlapped to solvent signal), 6.85 (1H, d, J=9.6 Hz), 4.93 (2H, s), 4.30-4.20 (1H, m), 4.20-4.00 (2H, m), 2.80-2.70 (3H, m), 2.15-2.05 (1H, m), 1.80-1.70 (1H, m), 1.70-1.50 (2H, m), 1.48 (9H, s). MS (ES$^+$) C$_{24}$H$_{28}$FN$_3$O$_3$ required: 425, found: 426 (M+H)$^+$.

Step 8: Methyl 2-{4-[1-(tert-butoxycarbonyl)piperidin-3-yl]phenyl}-6-fluoro-2H-indazole-4-carboxylate (F8)

(F8) was prepared following the general procedure reported in Example 3 step 6 and 7 and was purified by flash column chromatography on silica (EtOAc/Petroleum ether 2:3) yielding (39%) the title compound as a pale yellow foam. $^1$H NMR (400 MHz, CDCl$_3$, 300K) δ 8.88 (1H, s), 7.85 (2H, d, J=8.1 Hz), 7.68 (1H, d, J=9.2 Hz), 7.57 (1H, d, J=9.0 Hz), 7.38 (2H, d, J=8.3 Hz), 4.30-4.10 (2H, m), 3.99 (3H, s), 2.80-2.70 (3H, m), 2.15-2.00 (1H, m), 1.80-1.70 (1H, m), 1.70-1.50 (2H, m), 1.47 (9H, s). MS (ES$^+$) C$_{25}$H$_{28}$FN$_3$O$_4$ required: 453, found: 454 (M+H)$^+$.

Step 9: methyl 3-bromo-2-{4-[1-(tert-butoxycarbonyl)piperidin-3-yl]phenyl}-6-fluoro-2H-indazole-4-carboxylate (F9)

(F8) was treated with Br$_2$ (1.2 eq.) following the general procedure reported in Example 3 step 8, then the reaction crude was diluted with DCM (0.2 M) and treated with Boc$_2$O (1.0 eq.) and TEA (1.0 eq.). The reaction mixture was stirred at RT for 1 h. Evaporation of the solvent gave a residue that was purified by flash chromatography column on silica (EtOAc/Petroleum ether 1:8 to 1:6) yielding (66%) the title compound as a white solid. $^1$H NMR (400 MHz, CDCl$_3$, 300K) δ 7.60-7.50 (4H, m), 7.48-7.41 (2H, m), 4.33-4.13 (2H, m), 4.04 (3H, s), 2.89-2.76 (3H, m), 2.16-2.05 (1H, m), 1.86-1.78 (1H, m), 1.75-1.61 (2H, m), 1.51 (9H, s). MS (ES$^+$) C$_{25}$H$_{27}$BrFN$_3$O$_4$ required: 531/533, found: 532/534 (M+H)$^+$.

Step 10: Methyl 2-{4-[1-(tert-butoxycarbonyl)piperidin-3-yl]phenyl}-3-[(Z)-2-ethoxyvinyl]-6-fluoro-2H-indazole-4-carboxylate (F10)

(F10) was prepared following a modified procedure of the general experimental reported in Example 3 step 9 where CsF (2.1 eq.) was added to the initial reaction mixture. After work-up, evaporation of the solvent gave a residue that was purified by flash chromatography column on silica (EtOAc/Petroleum ether 1:10 to 1:3) yielding (84%) the title compound as a yellow oil. $^1$H NMR (400 MHz, CDCl$_3$, 300K) δ 7.49 (2H, d, J=7.5 Hz), 7.42 (2H, d, J=8.8 Hz), 7.28 (2H, d, J=7.9 Hz), 6.08 (1H, d, J=6.4 Hz), 5.68 (1H, d, J=6.6 Hz), 4.28-4.00 (2H, m), 3.86 (3H, s), 3.57-3.47 (2H, m), 2.79-2.64 (3H, m), 2.08-1.93 (1H, m), 1.76-1.68 (1H, m), 1.64-1.50 (2H, m), 1.41 (9H, s), 0.92 (3H, d, J=7.0 Hz). MS (ES$^+$) C$_{29}$H$_{34}$FN$_3$O$_5$ requires: 523, found: 524 (M+H)$^+$.

Step 11: Methyl 2-{4-[1-(tert-butoxycarbonyl)piperidin-3-yl]phenyl}-6-fluoro-3-(2-oxoethyl)-2H-indazole-4-carboxylate (F11)

(F11) was prepared following the general procedure reported in Example 3 step 10 and was used in the next step without further purification. $^1$H NMR (400 MHz, DMSO-d$_6$, 300K) δ 9.77 (1H, s), 7.86 (1H, d, J=9 Hz), 7.70 (1H, d, J=10.3 Hz), 7.63-7.50 (4H, m), 4.41 (2H, s), 4.15-4.00 (2H, m), 3.94 (3H, s), 2.97-2.78 (3H, m), 2.10-1.95 (1H, m), 1.86-1.74 (1H, m), 1.72-1.59 (2H, m), 1.48 (9H, s). MS (ES$^+$) C$_{27}$H$_{30}$FN$_3$O$_5$ requires: 495, found: 496 (M+H)$^+$.

Step 12: Methyl 2-{4-[1-(tert-butoxycarbonyl)piperidin-3-yl]phenyl}-3-{2-[(2,4-dimethoxybenzyl)amino]ethyl}-6-fluoro-2H-indazole-4-carboxylate (F12)

(F12) was prepared following the general procedure reported in Example 3 step 11. Evaporation of the solvent gave a residue that was purified by flash chromatography column on silica (EtOAc/Petroleum ether 1:1 and EtOAc) yielding (61% over two steps) the title compound as a yellow solid. $^1$H NMR (400 MHz, CDCl$_3$, 300K) δ 7.67 (1H, d, J=9.4 Hz), 7.53 (1H, d, J=8.1 Hz), 7.42 (2H, d, J=7.7 Hz), 7.35 (2H, d, J=7.4 Hz), 7.11 (2H, d, J=8.1 Hz), 6.44 (1H, d, J=8.4 Hz), 6.40 (1H, s), 4.35-4.05 (4H, m), 3.97 (3H, s), 3.81 (3H, s), 3.74 (3H, s), 3.70-3.61 (2H, m), 3.18-3.09 (2H, m), 2.88-2.72 (3H, m), 2.16-2.07 (1H, m), 1.85-1.76 (1H, m), 1.76-1.55 (2H, m), 1.48 (9H, s). MS (ES$^+$) C$_{36}$H$_{43}$FN$_4$O$_6$ requires: 646, found: 647 (M+H)$^+$.

Step 13: tert-Butyl 3-{4-[5-(2,4-dimethoxybenzyl)-8-fluoro-6-oxo-3,4,5,6-tetrahydro-2H-azepino[5,4,3-cd]indazol-2-yl]phenyl}piperidine-1-carboxylate (F13)

To a solution of (F12) in THF/H$_2$O (1:1, 0.2 M), LiOH (1.5 eq.) was added and the reaction mixture was stirred at RT for 5.5 h. Then, the reaction mixture was quenched by the addition of 6N HCl and the aqueous phase was separated and extracted several times with DCM. The combined organic layers were washed with brine and dried (Na$_2$SO$_4$). The solvent was evaporated to dryness to afford (2-{4-[1-(tert-butoxycarbonyl)piperidin-3-yl]phenyl}-3-{2-[(2,4-dimethoxybenzyl)amino]ethyl}-6-fluoro-2H-indazole-4-carboxylic acid (MS (ES$^+$) C$_{35}$H$_{41}$FN$_4$O$_6$ requires: 632, found: 633 (M+H$^+$)) which was dissolved in DMF (0.034 M). The resulting solution was treated with HATU (1.0 eq.) and DIEA (1.0 eq.). The reaction mixture was stirred at RT for 1 h. Then, the resulting mixture was pardoned between 1N HCl solution and DCM. The aqueous phase was separated and extracted several times with DCM. The combined organic layers were washed with brine and dried (Na$_2$SO$_4$). Evaporation of the solvent gave a residue that was purified by flash chromatography column on silica (EtOAc/Petroleum ether 3:7 to 1:1) yielding (53% over two steps) the title compound as a white powder. $^1$H NMR (400 MHz, CDCl$_3$, 300K) δ 7.80 (1H, d, J=9.8 Hz), 7.50 (2H, d, J=7.6 Hz), 7.44 (1H, d, J=9.2 Hz), 7.38 (2H, d, J=8.1 Hz), 7.34 (1H, d, J=8.8 Hz), 6.55-6.40 (2H, m), 4.90-4.70 (2H, m), 4.30-4.00 (2H, m), 3.82 (6H, s), 3.80-3.70 (2H, m), 3.20-3.00 (2H, m), 2.80-2.70 (3H, m), 2.10-2.00 (1H, m), 1.80-1.70 (1H, m), 1.70-1.60 (2H, m), 1.48 (9H, s). MS (ES$^+$) C$_{35}$H$_{39}$FN$_4$O$_5$ requires: 614, found: 615 (M+H)$^+$.

Step 14: 3-[4-(8-Fluoro-6-oxo-3,4,5,6-tetrahydro-2H-azepino[5,4,3-cd]indazol-2-yl)phenyl]piperidinium trifluoroacetate (F14); 8-fluoro-2-{4-[(3R)-piperidin-3-yl]phenyl}-2,3,4,5-tetrahydro-6H-azepino[5,4,3-cd]indazol-6-one (F15); and 8-fluoro-2-{4-[(3S)-piperidin-3-yl]phenyl}-2,3,4,5-tetrahydro-6H-azepino[5,4,3-cd]indazol-6-one (F16)

(F13) was deprotected following the general procedure reported in Example 1 step 7 yielding (55%) (F14) as a white powder. $^1$H NMR (400 MHz, CD$_3$CN, 300K) δ 9.10-8.70 (2H, bs), 7.70-7.60 (3H, m), 7.60-7.40 (3H, m), 7.00-6.90 (1H, m), 3.60-3.50 (2H, m), 3.50-3.40 (2H, m), 3.30-3.20 (1H, m), 3.20-3.10 (2H, m), 3.10-2.90 (2H, m), 2.10-2.00 (3H, m), 1.90-1.70 (1H, m). MS (ES$^+$) C$_{21}$H$_{22}$FN$_4$O requires: 364, found: 365 (M+H)$^+$.

(F14) was separated by chiral SFC (column: Chiralcel OJ-H, 1×25 mm, flow: 10 ml/min, T$_{col}$: 35° C., P$_{col}$: 100 bar, modifier: 50% (MeOH+4% Et$_2$NH)), using CO$_2$ as supercritical eluent, affording both pure enantiomers as free base.

The first eluted enantiomer, retention time (SFC): 4.30 min, was obtained as a white powder. $^1$H NMR (400 MHz, DMSO-d$_6$, 300K) 8.41 (1H, t, J=5.5 Hz), 7.67-7.63 (3H, m), 7.53-7.46 (3H, m), 3.48 (2H, bs), 3.25 (2H, bs), 3.04-2.94

(2H, m), 2.76-2.70 (1H, m), 2.60-2.48 (2H, m), 1.96-1.90 (1H, m), 1.70-1.48 (3H, m). MS (ES$^+$) $C_{21}H_{22}FN_4O$ requires: 364, found: 365 (M+H)$^+$.

The second eluted enantiomer, retention time (SFC): 6.71 min, was obtained as a white powder. $^1$H NMR (400 MHz, DMSO-d$_6$, 300K) 8.41 (1H, t, J=5.5 Hz), 7.67-7.63 (3H, m), 7.53-7.46 (3H, m), 3.48 (2H, bs), 3.25 (2H, bs), 3.04-2.94 (2H, m), 2.76-2.70 (1H, m), 2.60-2.48 (2H, m), 1.96-1.90 (1H, m), 1.70-1.48 (3H, m). MS (ES$^+$) $C_{21}H_{22}FN_4O$ requires: 364, found: 365 (M+H)$^+$.

EXAMPLE 7

N$^2$,N$^2$-Dimethyl-N-[4-(1-oxo-1,2,3,4-tetrahydroazepino[3,4,5-hi]indolizin-5-yl)phenyl]glycinamide (G7)

Step 1: Benzyl prop-2-yn-1-ylcarbamate (G1)

To a solution of propargylamine and triethylamine (1.3 eq.) in DCM (3 M) at 0° C., it was added dropwise a solution of benzyl chloroformate (1.1 eq.) in DCM (5 M). The reaction mixture was stirred at RT for 2 h. After evaporation of the solvent the resulting residue was purified by flash column chromatography on silica (EtOAc/Petroleum ether 1:10) to yield (56%) the title compound. $^1$H NMR (300 MHz, CDCl$_3$, 300K) δ 7.3 (5H, s), 5.29 (2H, s), 5.0 (1H, bs), 3.85 (2H, d, J=3.3 Hz), 2.21 (1H, m). MS (ES$^+$) $C_{11}H_{11}NO_2$ requires: 189, found: 190 (M+H)$^+$.

Step 2: Methyl 2-bromonicotinate (G2)

A solution of CH$_2$N$_2$ (4 eq.) in Et$_2$O (1 M) was added dropwise to a solution of 2-bromonicotinic acid in THF (0.5 M) at RT. The reaction mixture was stirred at room temperature overnight, then quenched by dropwise addition of AcOH (4 eq.). The organic phase was washed with water and brine and dried (MgSO$_4$). Evaporation of the solvent yielded (75%) the title compound which was used in the next step without further purification. $^1$H NMR (300 MHz, CDCl$_3$, 300K) δ 8.47 (1H, dd, J=4.8 Hz, 2.1 Hz), 8.07 (1H, dd, J=7.8 Hz, 2.1 Hz), 7.35 (1H, dd, J=7.5 Hz, 4.5 Hz), 3.93 (3H, s).

Step 3: Methyl 2-(3-{[(benzyloxy)carbonyl]amino}prop-1-yn-1-yl)nicotinate (G3)

CuI (0.047 eq.) was added to a stirred solution of (G2) in triethylamine (0.27 M) at RT, and the mixture was degassed by passing a stream of N$_2$ through the solution for 15 min. After cooling to 0° C., (G1) (1.05 eq.) was added, followed by dichlorobis(triphenylphosphine)palladium (II) (0.023 eq.). After stirring at 0° C. for 1 h, the reaction mixture was allowed to warm to RT and then stirred for an additional 8 h. The mixture was filtered through a pad of celite and the solvent was removed in vacuo. Then, the residue was purified by flash column chromatography on silica (EtOAc/Petroleum ether 2:1) to yield (86%) the title compound. $^1$H NMR (400 MHz, DMSO-d$_6$, 300K) δ 8.67 (1H, s), 8.20 (1H, d, J=8.0 Hz), 7.31 (6H, m), 5.28 (1H, bs), 5.13 (2H, s), 4.31 (2H, s), 3.89 (3H, s). MS (ES$^+$) $C_{18}H_{16}N_2O_4$ requires: 324, found: 325 (M+H)$^+$.

Step 4: 6,7,8,9-Tetrahydro-5H-pyrido[3,2-c]azepin-5-one (G4)

Pd on carbon (10 wt %) was added to a solution of (G3) in MeOH (0.2 M), and the reaction mixture was stirred under H$_2$ atmosphere (1 atm.) at RT for 18 h. The catalyst was removed by filtration through a pad of celite and the resulting solution was heated to reflux for 5 h. After cooling down, the solvent was removed in vacuo and the residue was purified by flash column chromatography on silica (DCM/MeOH 20:1) to yield (69%) the title compound. $^1$H NMR (300 MHz, CDCl$_3$, 300K) δ 8.68 (1H, m), 8.18 (1H, m), 7.50 (1H, m), 6.88 (1H, s), 3.15 (4H, m), 2.12 (2H, m). MS (ES$^+$) $C_9H_{10}N_2O$ requires: 162, found: 163 (M+H)$^+$.

Step 5: 5-(4-Nitrophenyl)-3,4-dihydroazepino[3,4,5-hi]indolizin-1(2H)-one (G5)

A mixture of (G4) and 2-bromo-1-(4-nitrophenyl)ethanone (1.17 eq.) in MeOH (0.33 M) was heated to reflux for 24 h. After cooling down, CH$_3$ONa (4 eq.) and toluene were added. Then, the reaction mixture was heated to reflux for another 24 h. After cooling down, solvent was removed in vacuo and the resulting residue was purified by flash column chromatography on silica (DCM/MeOH 200:1) to yield (22%) the title compound. $^1$H NMR (300 MHz, DMSO-d$_6$, 300K) δ 8.42 (1H, d, J=6.9 Hz), 8.27 (3H, m), 8.02 (1H, s), 7.76 (2H, d, J=8.1 Hz), 7.40 (1H, d, J=6.6 Hz), 6.68 (1H, t, J=6.9 Hz), 3.30 (2H, m), 3.04 (2H, m). MS (ES$^-$) $C_{17}H_{13}N_3O_3$ requires: 307, found: 308 (M+H)$^+$.

Step 6: 5-(4-Aminophenyl)-3,4-dihydroazepino[3,4,5-hi]indolizin-1(2H)-one (G6)

A suspension of (G5), iron powder (6 eq.) and NH$_4$Cl (10 eq.) in EtOH/H$_2$O (0.013 M) was heated to reflux for 3 h. After cooling down, the catalyst was removed off by filtration. The resulting filtrate was concentrated in vacuo giving a residue that was purified by flash column chromatography on silica to yield (81%) the title compound as a yellow solid. $^1$H NMR (400 MHz, CD$_3$OD, 300K) δ 8.68 (1H, d, J=6.8 Hz), 7.60 (1H, s), 7.45 (1H, d, J=6.8 Hz), 7.25 (2H, d, J=8.0 Hz), 6.82 (2H, d, J=8.0 Hz), 6.56 (1H, t, J=6.8 Hz), 3.52 (2H, m), 3.08 (2H, m). MS (ES$^+$) $C_{17}H_{15}N_3O$ requires: 277, found: 278 (M+H)$^+$.

Step 7: N$^2$,N$^2$-Dimethyl-N-[4-(1-oxo-1,2,3,4-tetrahydroazepino[3,4,5-hi]indolizin-5-yl)phenyl]glycinamide (G7)

A solution of (G6), N,N-dimethylglycine (2 eq.), HATU (0.15 eq.) and DIEA (3 eq.) in DMF (0.05 M) was stirred at RT overnight. The reaction mixture was concentrated in vacuo giving a residue that was purified by flash column chromatography on silica to yield (18%) the title compound. $^1$H NMR (300 MHz, CD$_3$OD, 300K) δ 8.26 (1H, d, J=6.8 Hz), 7.65 (3H, m), 7.48 (3H, m), 6.60 (1H, t, J=7.2 Hz), 3.54 (2H, bs), 3.20 (2H, s), 3.12 (2H, bs), 2.41 (6H, s). MS (ES$^+$ $C_{21}H_{22}N_4O_2$ requires: 362, found: 363 (M+H)$^+$.

The Examples in the following table were prepared according to the procedures described in the above Examples.

| Example | Name | Molecular Ion [M + H]$^+$ | Procedure of Example |
|---|---|---|---|
| 8 | N,N-dimethyl[4-(6-oxo-6,7,8,9-tetrahydro-2,7,9b-triazabenzo[cd]azulen-1-yl)phenyl]methanaminium trifluoroacetate | 321 | 1 |

| Example | Name | Molecular Ion [M + H]+ | Procedure of Example |
|---|---|---|---|
| 9 | N-[4-(6-oxo-6,7,8,9-tetrahydro-2,7,9b-triazabenzo[cd]azulen-1-yl)benzyl]propan-2-aminium trifluoroacetate | 335 | 1 |
| 10 | 2-[4-(6-oxo-6,7,8,9-tetrahydro-2,7,9b-triazabenzo[cd]azulen-1-yl)benzyl]-2,7-diazoniaspiro[4.5]decane bis(trifluoroacetate) | 416 | 1 |
| 11 | 1-methyl-4-({[4-(6-oxo-6,7,8,9-tetrahydro-2,7,9b-tiazabenzo[cd]azulen-1-yl)benzyl]ammonio}methyl)piperidinium bis(trifluoroacetate) | 404 | 1 |
| 12 | N,N-dimethyl[4-(5-oxo-4,5-dihydro-3H-1,4,8b-triazaacenaphthylen-2-yl)phenyl]methanaminium trifluoroacetate | 307 | 2 |
| 13 | 2-[4-(5-oxo-4,5-dihydro-3H-1,4,8b-triazaacenaphthylen-2-yl)benzyl]-2,7-diazoniaspiro[4.5]decane bis(trifluoroacetate) | 402 | 2 |
| 14 | 1-methyl-4-({[4-(5-oxo-4,5-dihydro-3H-1,4,8b-triazaacenaphthylen-2-yl)benzyl]ammonio}methyl)piperidinium bis(trifluoroacetate) | 390 | 2 |
| 15 | N-[4-(5-oxo-4,5-dihydro-3H-1,4,8b-triazaacenaphthylen-2-yl)benzyl]propan-2-aminium trifluoroacetate | 321 | 2 |
| 16 | 2-[4-(6-oxo-3,4,5,6-tetrahydro-2H-azepino[5,4,3-cd]indazol-2-yl)benzyl]-2,7-diazoniaspiro[4.5]decane bis(trifluoroacetate) | 416 | 3 |
| 17 | 5-phenyl-3,4-dihydroazepino[3,4,5-hi]indolizin-1(2H)-one | 263 | 7 |
| 18 | ethyl 4-(1-oxo-1,2,3,4-tetrahydroazepino[3,4,5-hi]indolizin-5-yl)benzoate | 335 | 7 |
| 19 | 5-(4-nitrophenyl)-3,4-dihydroazepino[3,4,5-hi]indolizin-1(2H)-one | 308 | 7 |
| 20 | 5-[4-(hydroxymethyl)phenyl]-3,4-dihydroazepino[3,4,5-hi]indolizin-1(2H)-one | 293 | 7 |
| 21 | N-[4-(1-oxo-1,2,3,4-tetrahydroazepino[3,4,5-hi]indolizin-5-yl)phenyl]nicotinamide | 383 | 7 |
| 22 | N-[4-(1-oxo-1,2,3,4-tetrahydroazepino[3,4,5-hi]indolizin-5-yl)phenyl]pyridine-2-carboxamide | 383 | 7 |
| 23 | N-[4-(1-oxo-1,2,3,4-tetrahydroazepino[3,4,5-hi]indolizin-5-yl)phenyl]-2-pyrrolidin-1-ylacetamide | 389 | 7 |
| 24 | 1-methyl-N-[4-(1-oxo-1,2,3,4-tetrahydroazepino[3,4,5-hi]indolizin-5-yl)phenyl]piperidine-4-carboxamide | 403 | 7 |
| 25 | 3-({[4-(1-oxo-1,2,3,4-tetrahydroazepino[3,4,5-hi]indolizin-5-yl)phenyl]amino}carbonyl)azetidinium chloride | 361 | 7 |
| 26 | (3S)-1-methyl-N-[4-(1-oxo-1,2,3,4-tetrahydroazepino[3,4,5-hi]indolizin-5-yl)phenyl]piperidine-3-carboxamide | 403 | 7 |
| 27 | (3R)-1-methyl-N-[4-(1-oxo-1,2,3,4-tetrahydroazepino[3,4,5-hi]indolizin-5-yl)phenyl]piperidine-3-carboxamide | 403 | 7 |
| 28 | (2S)-1-methyl-N-[4-(1-oxo-1,2,3,4-tetrahydroazepino[3,4,5-hi]indolizin-5-yl)phenyl]piperidine-2-carboxamide | 403 | 7 |
| 29 | (2R)-1-methyl-N-[4-(1-oxo-1,2,3,4-tetrahydroazepino[3,4,5-hi]indolizin-5-yl)phenyl]piperidine-2-carboxamide | 403 | 7 |
| 30 | 5-{4-[(dimethylamino)methyl]phenyl}-3,4-dihydroazepino[3,4,5-hi]indolizin-1(2H)-one | 320 | 7 |
| 31 | 5-{4-[(methylamino)methyl]phenyl}-3,4-dihydroazepino[3,4,5-hi]indolizin-1(2H)-one | 306 | 7 |
| 32 | 5-{4-[(4-methylpiperazin-1-yl)methyl]phenyl}-3,4-dihydroazepino[3,4,5-hi]indolizin-1(2H)-one | 375 | 7 |
| 33 | 5-{4-[(isopropylamino)methyl]phenyl}-3,4-dihydroazepino[3,4,5-hi]indolizin-1(2H)-one | 334 | 7 |
| 34 | 5-(4-{[(2-hydroxyethyl)amino]methyl}phenyl)-3,4-dihydroazepino[3,4,5-hi]indolizin-1(2H)-one | 336 | 7 |

The invention claimed is:

1. A compound of formula I:

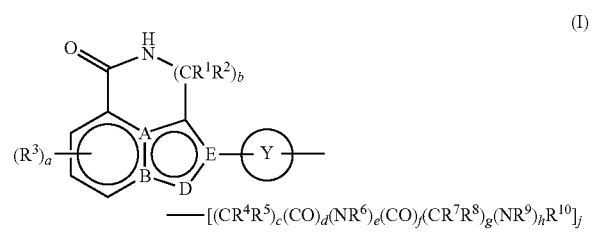

——[(CR⁴R⁵)c(CO)d(NR⁶)e(CO)f(CR⁷R⁸)g(NR⁹)hR¹⁰]j wherein:
a is 0, 1, 2 or 3;
b is 1 or 2;
each c is independently 0, 1, 2, 3, 4, 5 or 6;
each d is independently 0 or 1;
each e is independently 0 or 1;
each f is independently 0 or 1;
each g is independently 0, 1, 2, 3, 4, 5 or 6;
each h is independently 0 or 1;
j is 0, 1, 20r 3;
A is either C or CH as the case may be; one of B, D and E is N and the others are independently N or either C or CH as the case may be, provided that when D is N then at least one of B and E is N;
each of $R^1$ and $R^2$ is independently hydrogen or $C_{1-6}$alkyl;
each $R^3$ is independently hydroxy, halogen, cyano, $C_{1-6}$alkyl, halo$C_{1-6}$alkyl, $C_{1-6}$alkoxy or halo$C_{1-6}$alkoxy;
each of $R^4$, $R^5$, $R^7$ and $R^8$ is independently hydrogen, $C_{1-6}$alkyl or halo $C_{1-6}$alkyl;
each of $R^6$ and $R^9$ is independently hydrogen, $C_{1-6}$alkyl or $C_{3-10}$cycloalkyl;
each $R^{10}$ is independently hydrogen, hydroxy, cyano, halogen, $C_{1-6}$alkyl, $C_{2-10}$alkenyl, halo$C_{1-6}$alkyl, hydroxy$C_{1-6}$ alkyl, $C_{1-6}$alkylcarbonyl, $C_{1-6}$alkoxy, halo$C_{1-6}$alkoxy, $C_{1-6}$alkoxycarbonyl, carboxy, nitro or a ring which is: $C_{6-10}$aryl; $C_{6-10}$aryloxy; $C_{6-10}$arylcarbonyl; $C_{3-10}$cycloalkyl; oxetanyl; azetidinyl; a 5 or 6 membered saturated or partially saturated heterocyclic ring containing one, two or three heteroatoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 N atoms; or a 7-15 membered unsaturated, partially saturated or saturated heterocyclic ring containing 1, 2, 3 or 4 heteroatoms independently selected from N, O and S; any of which rings being optionally substituted by one, two or three groups independently selected from $(CH_2)_x R^{11}$;

each x is independently 0, 1, 2, 3, 4, 5 or 6;

each $R^{11}$ is independently hydroxy, oxo, cyano, halogen, $C_{1-6}$alkyl, $C_{2-10}$alkenyl, halo$C_{1-6}$alkyl, $C_{1-6}$alkylcarbonyl, $C_{1-6}$alkoxy, halo$C_{1-6}$alkoxy, hydroxy$C_{1-6}$alkyl, $C_{1-6}$alkoxycarbonyl, carboxy, $NR^a R^b$, $CONR^a R^b$, $S(O)_r R^c$ or a ring which is: $C_{6-10}$aryl; $C_{6-10}$aryl$C_{1-6}$alkyl; oxetanyl; azetidinyl; a 5, 6 or 7 membered saturated or partially saturated heterocyclic ring containing one, two or three heteroatoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-10 membered unsaturated or partially saturated heterocyclic ring containing 1, 2, 3 or 4 heteroatoms independently selected from N, O and S;

any of which rings being optionally substituted by one, two or three groups independently selected from hydroxy, cyano, halogen, $C_{1-6}$alkyl, $C_{1-6}$alkoxy, $C_{2-10}$alkenyl, halo$C_{1-6}$alkyl, amino, $C_{1-6}$alkylamino and di($C_{1-6}$alkyl)amino;

each of $R^a$ and $R^b$ is independently hydrogen, $C_{1-6}$alkyl, $C_{1-6}$alkylcarbonyl, halo$C_{1-6}$alkyl, hydroxy$C_{1-6}$alkyl, $S(O)_r R^c$ or $S(O)_r N(R^d)_2$; or $R^a$ and $R^b$ together with the N atom to which they are attached form an azetidinyl ring or a 5, 6 or 7 membered saturated or partially saturated heterocycle containing one, two or three N atoms and zero or one O atom, the ring being optionally substituted by one, two or three groups independently selected from hydroxy, cyano, halogen, $C_{1-6}$alkyl, $C_{1-6}$alkoxy, $C_{2-10}$alkenyl and halo$C_{1-6}$alkyl;

r is 0, 1 or 2;

$R^c$ is $C_{1-6}$alkyl, $C_{6-10}$aryl, oxetanyl, azetidinyl, a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-10 membered unsaturated or partially saturated heterocyclic ring containing 1, 2, 3 or 4 heteroatoms independently selected from N, O and S; any of which rings being optionally substituted by one, two or three groups independently selected from hydroxy, cyano, halogen, $C_{1-6}$alkyl, $C_{2-10}$alkenyl and halo$C_{1-6}$alkyl;

each $R^d$ is independently hydrogen or $C_{1-6}$alkyl;

Y is $C_{6-10}$aryl, a 5 membered unsaturated heterocycle containing 1, 2, 3 or 4 heteroatoms independently selected from O, N and S, but not more than one of which is O or S, a 6 membered unsaturated heterocycle containing 1, 2 or 3 N atoms or a 7-10 membered unsaturated heterocyclic ring containing 1, 2, 3 or 4 heteroatoms independently selected from N, O and S;

or a pharmaceutically acceptable salt, stereoisomer or tautomer thereof.

2. A compound of claim 1 of formula III:

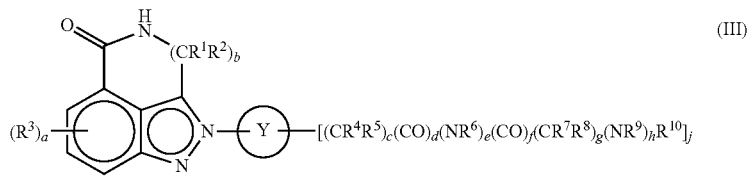

wherein all other variables are as defined in claim 1; or a pharmaceutically acceptable salt, stereoisomer or tautomer thereof.

3. A compound of claim 1 of formula IV:

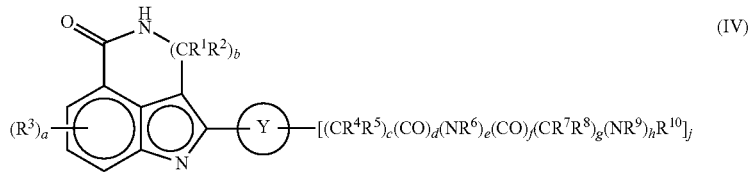

wherein all other variables are as defined in claim 1; or a pharmaceutically acceptable salt, stereoisomer or tautomer thereof.

4. A compound of claim 1 of formula V:

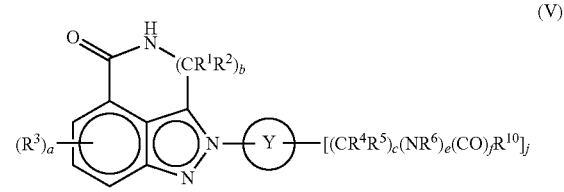

wherein all other variables are as defined in claim 1; or a pharmaceutically acceptable salt, stereoisomer or tautomer thereof.

5. A compound of claim 4 wherein Y is phenyl.

6. A compound of claim 4 wherein a is 0 or 1 and $R^3$ is halo$C_{1-6}$alkyl or halogen.

7. A compound of claim 4 wherein $R^{10}$ is hydroxy, $C_{1-6}$alkyl, $C_{1-6}$alkoxy, nitro or a ring which is: azetidinyl, a 5 or 6 membered saturated or partially saturated heterocyclic ring containing one, two or three heteroatoms independently selected from N, O and S, a 6 membered heteroaromatic ring containing 1, 2 or 3 N atoms or a 7 to 10 membered saturated or partially saturated heterocyclic ring containing 1, 2, 3 or 4 heteroatoms independently selected from N, O and S; any of which rings being optionally substituted by one, two or three groups independently selected from $(CH_2)_xR^{11}$.

8. A compound of claim 4 wherein x is 0 and $R^{11}$ is $C_{1-6}$alkyl.

9. A compound of claim 4 wherein $R^{10}$ is methyl, isopropyl, diazoniaspiro[4.5]decanyl, methylpiperidinyl, ethoxy, nitro, hydroxy, pyridinyl, pyrrolidinyl, azetidinyl, methylpiperazinyl or piperidinyl.

10. A pharmaceutical composition comprising a compound of claim 1, or a pharmaceutically acceptable salt, stereoisomer or tautomer thereof in association with a pharmaceutically acceptable carrier.

11. A compound according to claim 1 which is selected from:

- N-Methyl[4-(6-oxo-3,4,5,6-tetrahydro-2H-azepino[5,4,3-cd]indazol-2-yl)phenyl]methanaminium trifluoroacetate;
- N,N-Dimethyl[4-(6-oxo-3,4,5,6-tetrahydro-2H-azepino[5,4,3-cd]indazol-2-yl)phenyl]methanaminium trifluoroacetate;
- $N^2,N^2$-Dimethyl-N-[4-(1-oxo-1,2,3,4-tetrahydroazepino[3,4,5-hi]indolizin-5-yl)phenyl]glycinamide;
- 3-[4-(8-Fluoro-6-oxo-3,4,5,6-tetrahydro-2H-azepino[5,4,3-cd]indazol-2-yl)phenyl]piperidinium trifluoroacetate;
- 8-fluoro-2-{4-[(3R)-piperidin-3-yl]phenyl}-2,3,4,5-tetrahydro-6H-azepino[5,4,3-cd]indazol-6-one;
- 8-fluoro-2-{4-(3S)-piperidin-3-yl]phenyl}-2,3,4,5-tetrahydro-6H-azepino[5,4,3-cd]indazol-6-one;
- 2-[4-(6-oxo-3,4,5,6-tetrahydro-2H-azepino[5,4,3-cd]indazol-2-yl)benzyl]-2,7-diazoniaspiro[4.5]decane bis(trifluoroacetate);
- [4-(8-fluoro-6-oxo-3,4,5,6-tetrahydro-2H-azepino[5,4,3-cd]indazol-2-yl)phenyl]-N,N-dimethylmethanaminium trifluoroacetate;
- 5-phenyl-3,4-dihydroazepino[3,4,5-hi]indolizin-1(2H)-one;
- ethyl 4-(1-oxo-1,2,3,4-tetrahydroazepino[3,4,5-hi]indolizin-5-yl)benzoate;
- 5-(4-nitrophenyl)-3,4-dihydroazepino[3,4,5-hi]indolizin-1(2H)-one;
- 5-[4-(hydroxymethyl)phenyl]-3,4-dihydroazepino[3,4,5-hi]indolizin-1(2H)-one;
- N-[4-(1-oxo-1,2,3,4-tetrahydroazepino[3,4,5-hi]indolizin-5-yl)phenyl]nicotinamide;
- N-[4-(1-oxo-1,2,3,4-tetrahydroazepino[3,4,5-hi]indolizin-5-yl)phenyl]pyridine-2-carboxamide;
- N-[4-(1-oxo-1,2,3,4-tetrahydroazepino [3,4,5-hi]indolizin-5-yl)phenyl]-2-pyrrolidin-1-ylacetamide;
- 1-methyl-N-[4-(1-oxo-1,2,3,4-tetrahydroazepino[3,4,5-hi]indolizin-5-yl)phenyl]piperidine-4-carboxamide;
- 3-({[4-(1-oxo-1,2,3,4-tetrahydroazepino[3,4,5-hi]indolizin-5-yl)phenyl]amino}carbonyl)azetidinium chloride;
- (3S)-1-methyl-N-[4-(1-oxo-1,2,3,4-tetrahydroazepino[3,4,5-hi]indolizin-5-yl)phenyl]piperidine-3-carboxamide;
- (3R)-1-methyl-N-[4-(1-oxo-1,2,3,4-tetrahydroazepino[3,4,5-hi]indolizin-5-yl)phenyl]piperidine-3-carboxamide;
- (2S)-1-methyl-N-[4-(1-oxo-1,2,3,4-tetrahydroazepino[3,4,5-hi]indolizin-5-yl)phenyl]piperidine-2-carboxamide;
- (2R)-1-methyl-N-[4-(1-oxo-1,2,3,4-tetrahydroazepino[3,4,5-hi]indolizin-5-yl)phenyl]piperidine-2-carboxamide;
- 5-{4-[(dimethylamino)methyl]phenyl}-3,4-dihydroazepino[3,4,5-hi]indolizin-1(2H)-one;
- 5-{4-[(methylamino)methyl]phenyl}-3,4-dihydroazepino[3,4,5-hi]indolizin-1(2H)-one;
- 5-{4-[(4-methylpiperazin-1-yl)methyl]phenyl}-3,4-dihydroazepino[3,4,5-hi]indolizin-1(2H)-one;
- 5-{4-[(isopropylamino)methyl]phenyl}-3,4-dihydroazepino[3,4,5-hi]indolizin-1(2H)-one; and
- 5-(4-{[(2-hydroxyethyl)amino]methyl}phenyl)-3,4-dihydroazepino[3,4,5-hi]indolizin-1(2H)-one;

and pharmaceutically acceptable salts, free bases and tautomers thereof.

* * * * *